United States Patent
Abramovitch et al.

(10) Patent No.: US 11,246,912 B2
(45) Date of Patent: Feb. 15, 2022

(54) METHODS FOR TREATING AND DIAGNOSING METASTATIC LIVER CANCER

(71) Applicant: HADASIT MEDICAL RESEARCH SERVICES AND DEVELOPMENT LTD., Jerusalem (IL)

(72) Inventors: Rinat Abramovitch, Modiin (IL); Esther Goldlist, Maale Adumim (IL)

(73) Assignee: HADASIT MEDICAL RESEARCH SERVICES & DEVELOPMENT LTD., Jerusalem (IL)

( * ) Notice: Subject to any disclaimer, the term of this patent is extended or adjusted under 35 U.S.C. 154(b) by 0 days.

(21) Appl. No.: 16/641,517

(22) PCT Filed: Aug. 30, 2018

(86) PCT No.: PCT/IL2018/050963
§ 371 (c)(1),
(2) Date: Feb. 24, 2020

(87) PCT Pub. No.: WO2019/043708
PCT Pub. Date: Mar. 7, 2019

(65) Prior Publication Data
US 2021/0008169 A1    Jan. 14, 2021

Related U.S. Application Data

(60) Provisional application No. 62/551,889, filed on Aug. 30, 2017.

(51) Int. Cl.
*A61K 38/22* (2006.01)
*G01N 33/574* (2006.01)
*A61P 35/04* (2006.01)
*C12Q 1/6886* (2018.01)
*G01N 33/74* (2006.01)

(52) U.S. Cl.
CPC ............ *A61K 38/22* (2013.01); *A61P 35/04* (2018.01); *C12Q 1/6886* (2013.01); *G01N 33/57438* (2013.01); *G01N 33/74* (2013.01); *C12Q 2600/118* (2013.01); *C12Q 2600/158* (2013.01); *G01N 2333/575* (2013.01)

(58) Field of Classification Search
CPC ....... A61K 38/22; A61P 35/04; C12Q 1/6886; C12Q 2600/118; C12Q 2600/158; G01N 2333/575; G01N 33/57438; G01N 33/74
See application file for complete search history.

(56) References Cited

U.S. PATENT DOCUMENTS

| | | | |
|---|---|---|---|
| 4,235,871 | A | 11/1980 | Papahadjopoulos et al. |
| 4,501,728 | A | 2/1985 | Geho et al. |
| 4,837,028 | A | 6/1989 | Allen |
| 5,019,369 | A | 5/1991 | Presant et al. |
| 5,464,764 | A | 11/1995 | Capecchi et al. |
| 5,487,992 | A | 1/1996 | Capecchi et al. |
| 5,932,447 | A | 8/1999 | Siegall |
| 2009/0253619 | A1* | 10/2009 | Butler .................... C07K 16/18 514/1.1 |

OTHER PUBLICATIONS

Liang Li, A novel peptide adropin in cardiovascular diseases, Clinica Chimica Acta 453 (2016) 107-113, epub 2015.*
Feng Gao, Enho Mutations Causing Low Adropin: A Possible Pathomechanism of MPO-ANCA Associated Lung Injury, EBioMedicine 9 (2016) 324-335.*
Mechanisms of Carcinogenesis, section 3, 2008, international agency for research on cancer, pp. 1-37.*
Abramovitch, Rinat, et al, "Elucidating the effects of chronic liver inflammation on colorectal cancer metastatic dissemination". Cancer Microenvironment, Jun. 2018, vol. 11, No. Supplement 1.
Tuna, et al., "Effects of Chronic and Intermittent Calorie Restriction on Adropin Levels in Breast Cancer", Nutrition and Cancer, 2017, 69.7: 1003-1010.
Nergiz, et al. "Circulating adropin levels in patients with endometrium cancer", Gynecological Endocrinology, 2015, 31.9: 730-735.
Rao, et al., "G protein-coupled receptor GPR19 regulates E-cadherin expression and invasion of breast cancer cells", Biochimica et Biophysica Acta (BBA)Molecular Cell Research, 2017, 1864.7: 1318-1327.
International Search Report, International Application No. PCT/IL2018/050963, dated Nov. 7, 2018.

* cited by examiner

*Primary Examiner* — James H Alstrum-Acevedo
*Assistant Examiner* — Erinne R Dabkowski
(74) *Attorney, Agent, or Firm* — The Roy Gross Law Firm, LLC; Roy Gross

(57) ABSTRACT

The present invention is directed to a method for treating or preventing cancer in a subject in need thereof, comprising administering to the subject a therapeutically effective amount of an adropin stimulating agent. Further provided are a method and a kit for diagnosing or prognosing liver metastases in a subject.

6 Claims, 7 Drawing Sheets
Specification includes a Sequence Listing.

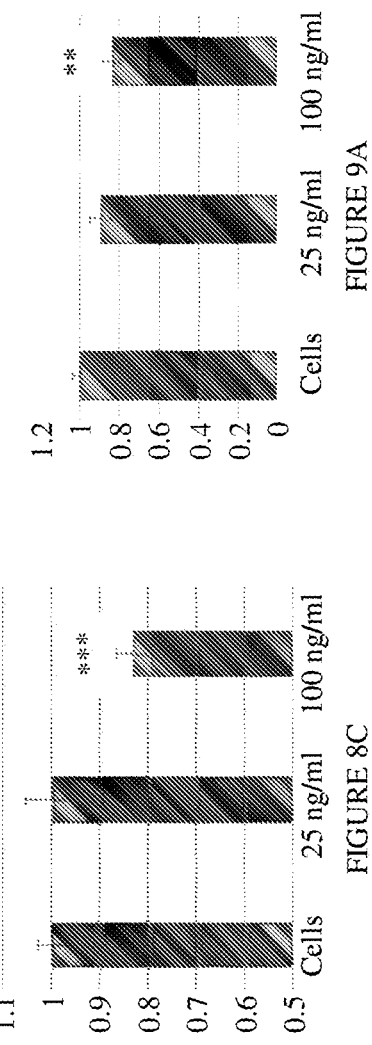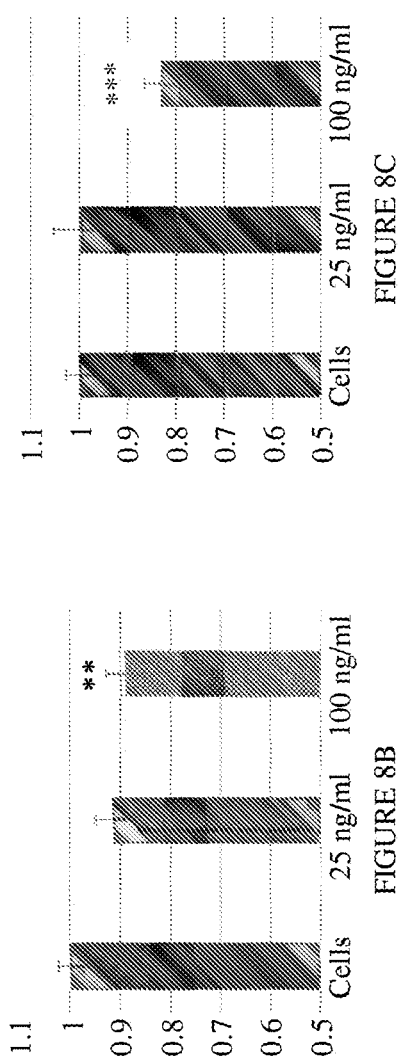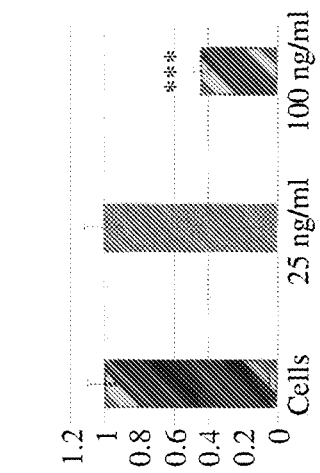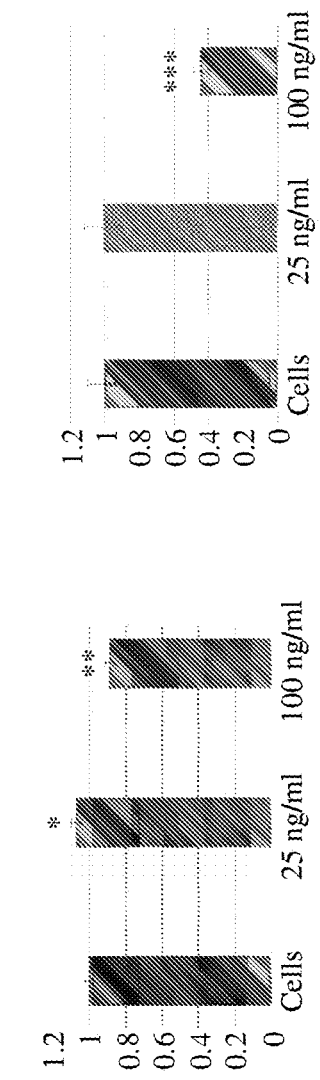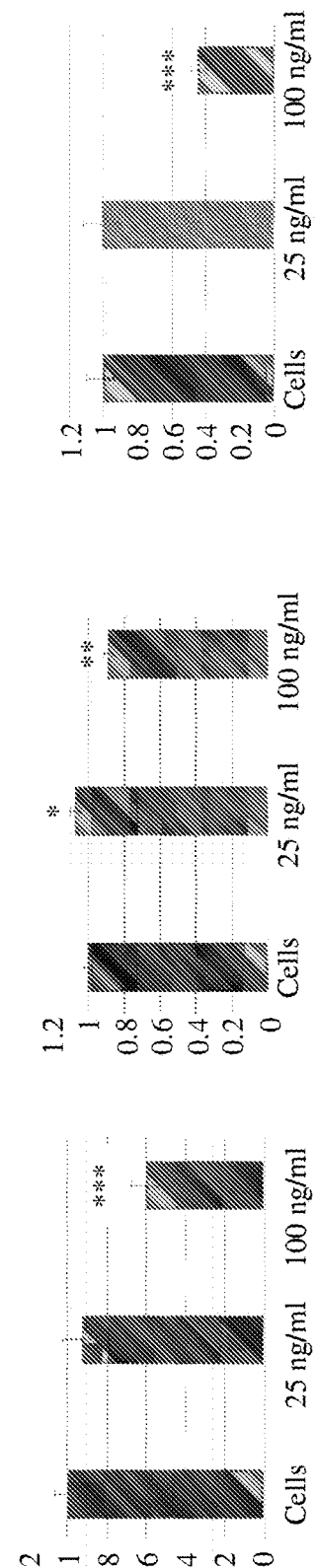

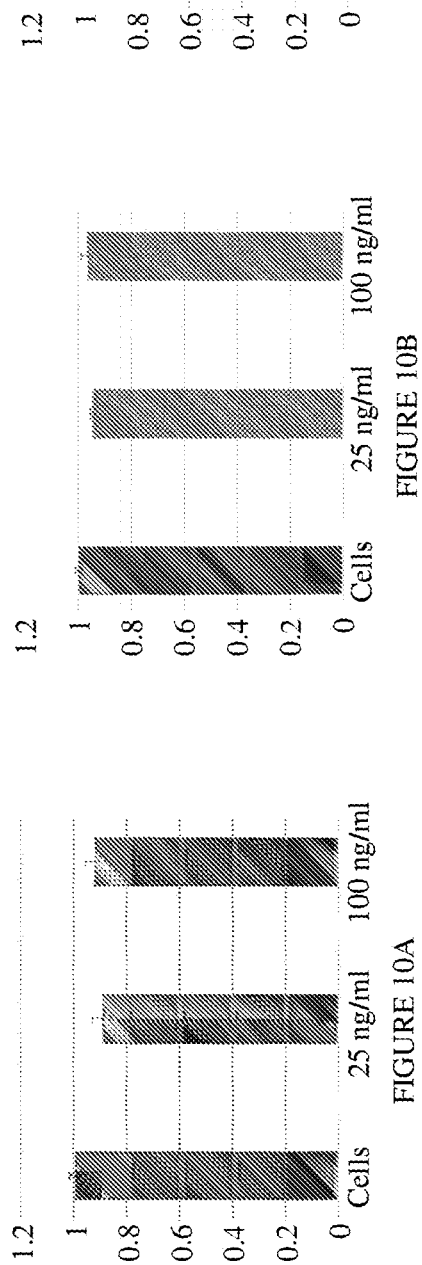
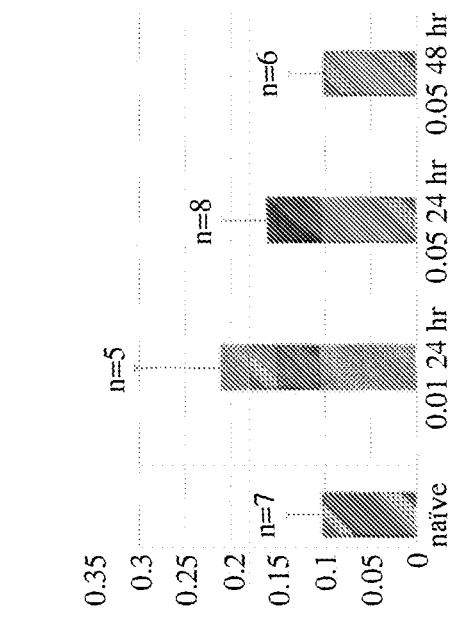
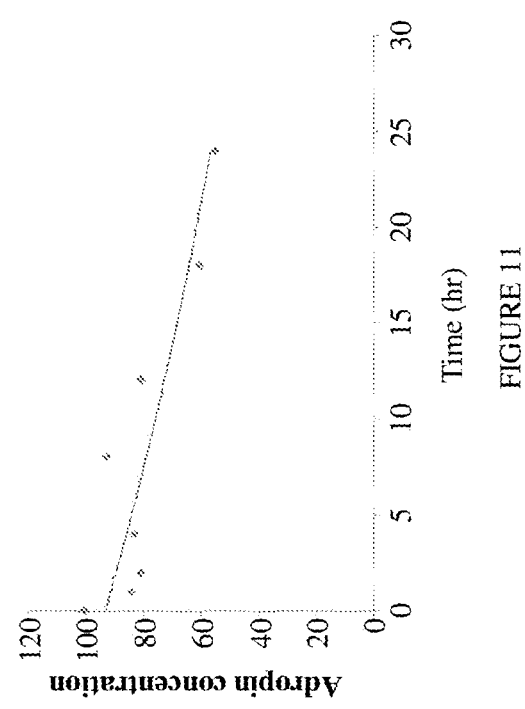

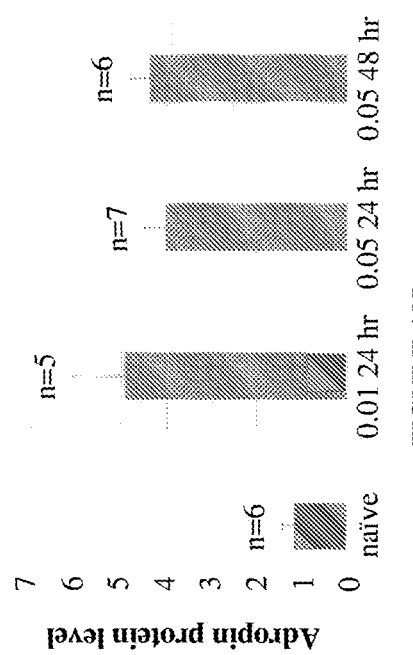
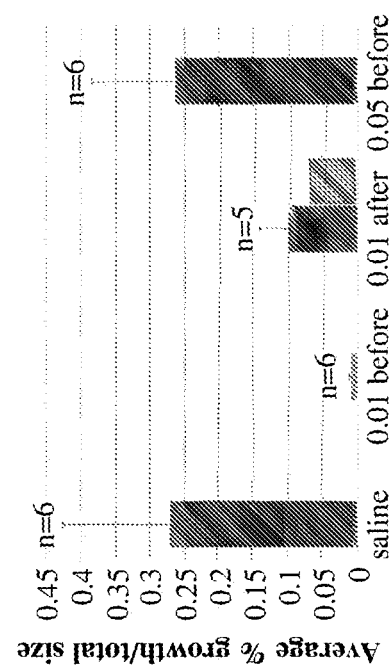
FIGURE 12B
FIGURE 13A
FIGURE 13B

```
                          SEQUENCE LISTING

<160> NUMBER OF SEQ ID NOS: 3

<210> SEQ ID NO 1
<211> LENGTH: 43
<212> TYPE: PRT
<213> ORGANISM: Artificial Sequence
<220> FEATURE:
<223> OTHER INFORMATION: Synthetic

<400> SEQUENCE: 1

Cys His Ser Arg Ser Ala Asp Val Asp Ser Leu Ser Glu Ser Ser Pro
1               5                   10                  15

Asn Ser Ser Pro Gly Pro Cys Pro Glu Lys Ala Pro Pro Gln Lys
            20                  25                  30

Pro Ser His Glu Gly Ser Tyr Leu Leu Gln Pro
        35                  40

<210> SEQ ID NO 2
<211> LENGTH: 42
<212> TYPE: PRT
<213> ORGANISM: Artificial Sequence
<220> FEATURE:
<223> OTHER INFORMATION: Synthetic

<400> SEQUENCE: 2

Cys His Ser Arg Ser Ala Asp Val Asp Ser Leu Ser Glu Ser Arg Thr
1               5                   10                  15

Gln Glu Ser Ala Cys Leu Glu Leu Asp Pro Ala Ala Gln Ser Leu Ala
            20                  25                  30

Ser Leu Ala Pro Ile Gly Ala Gln Trp Pro
        35                  40

<210> SEQ ID NO 3
<211> LENGTH: 1079
<212> TYPE: DNA
<213> ORGANISM: Homo sapiens

<400> SEQUENCE: 3
ggccgcggag gaggtgcggc cccaagggga ggaggtgccc gctcaccgca gaccgcccgc       60
ggcagaggcc gccccggtcg cgccgcggcg ggagcggccg gtggaggctg cgcggccgag      120
ggggagggcc gggggagcgg acgtcgcctc tgctggtctc ccacctcccg ccgcccccg       180 cccgcaggct cccaagcctt agtcggcgcc gagcatcccg ctgccccgga ccctcccgcg      240
ggcgcgcacc aggctcaact caggctcagg actgcaggta gacatctcca ctgcccagga      300
atcactgagc gtgcagacag cacagcctcc tctgaaggcc ggccatacca gagtcctgcc      360
tcggcatggg cctcaccatt gaggcagctc cactgtctgt gctggtctga gggtgctgcc      420
tgtcatgggg gcagccatct cccaggggc cctcatcgcc atcgtctgca acggtctcgt      480
gggcttcttg ctgctgctgc tctgggtcat cctctgctgg gcctgccatt ctcgctctgc      540
cgacgttgac tctctctctg aatccagtcc caactccagc cctggcccct gtcctgagaa      600 ggcccccacca ccccagaagc ccagccatga aggcagctac ctgctgcagc cctgaaggcc      660
cctggcctag cctggagccc aggacctaag tccacctcac ctagagcctg gaattaggat      720
```

```
cccagagttc agccagcctg gggtccagaa ctcaagagtc cgcctgcttg gagctggacc      780
cagcggccca gagtctagcc agcttggctc caataggagc tcagtggccc taaggagatg      840
ggcctggggt gggggcttat gagttggtgc tagagccagg gccatctgga ctatgctcca      900
tcccaagggc caagggtcag gggccgggtc cactctttcc ctaggctgag cacctctagg      960
ccctctaggt tggggaagca aactggaacc catggcaata ataggagggt gtccaggctg     1020
ggcccctccc ctggtcctcc cagtgtttgc tggataataa atggaactat ggctctaca     1079
```

METHODS FOR TREATING AND DIAGNOSING METASTATIC LIVER CANCER

CROSS REFERENCE

This application is National Phase of PCT Patent Application No. PCT/IL 2018/050963 having International filing date of Aug. 30, 2018, which claims the benefit of priority of U.S. Provisional Patent Application No. 62/551,889 filed on Aug. 30, 2017, the contents of which are incorporated herein by reference in their entirety.

FIELD OF INVENTION

The present invention is in the field of cancer therapy and diagnosis.

BACKGROUND OF THE INVENTION

The major cause of death in the western world is cancer and the majority of patients die as a result of metastatic dissemination. Liver metastases are more common than the primary tumors, and are most commonly of breast, ovarian, lung, or colorectal origin. The high incidence of hepatic metastases has been attributed to two mechanisms. First, the dual blood supply of the liver from the portal and systemic circulation increases the likelihood of metastatic deposits in the liver. Second, the hepatic sinusoidal epithelium has fenestrations that enable easier penetration of metastatic cells into the liver parenchyma.

Adropin is a regulatory secreted peptide involved in maintaining energy homeostasis, it is found in various tissues and body fluids and is known to be involved in carbohydrate-lipid metabolism, metabolic diseases, central nervous system function, endothelial function and cardiovascular disease.

SUMMARY OF THE INVENTION

The present invention, in some embodiments thereof, is directed to methods for treating and/or preventing cancer, including but not limited to liver metastases, comprising pharmaceutical compositions comprising adropin. Further, the present invention, in some embodiments thereof, is directed to a method for diagnosing and/or prognosing liver metastases.

According to one aspect, there is provided a method for treating or preventing cancer in a subject in need thereof, comprising administering to the subject a therapeutically effective amount of an adropin stimulating agent, wherein the agent increases the levels of expressed adropin in the subject, thereby treating or preventing cancer in the subject.

In some embodiments, the agent is an adropin polypeptide. In some embodiments, the agent is a polynucleotide encoding an adropin polypeptide.

In some embodiments, the adropin polypeptide comprises an amino acid sequence having at least 80% homology to SEQ ID NO: 1 (CHSRSADVDSLSESSPNS SPGPC-PEKAPPPQKPSHEGSYLLQP).

In some embodiments, the cancer is in an adropin-expressing organ. In some embodiments, the cancer is metastatic cancer. In some embodiments, the metastatic cancer is liver metastases.

In some embodiments, the increased adropin levels comprise increased RNA transcript levels, increased protein production levels, increased protein secretion levels, or any combination thereof.

In some embodiments, the treating comprises decreasing tumor size, decreasing metastases frequency, or a combination thereof.

In some embodiments, method further comprises the step of monitoring one or more symptoms selected from the group consisting of: tumor size, tumor growth, number of metastases, and size of metastases.

According to another aspect, there is provided a method for diagnosing or prognosing liver metastases in a subject, comprising the step of determining the expression level of adropin in a sample of the subject, wherein reduced adropin levels in the sample compared to control is indicative of liver metastases or severity thereof in the subject, thereby diagnosing or prognosing liver metastases in the subject.

In some embodiments, the sample is selected from the group consisting of: a liver sample or a bodily fluid.

In some embodiments, the control is adropin expression levels in a sample selected from the group consisting of: a tissue of a healthy subject, a benign tissue of said subject, and a tumor-neighboring or adjacent tissue of said subject.

In some embodiments, the determination of expression level of adropin is performed by one or more methods selected from the group consisting of: hybridization assay, polynucleotide amplification assay, and an immunoassay.

According to another aspect, there is provided a kit for diagnosing or prognosing liver metastases in a subject, comprising a molecular probe having specific affinity to adropin polypeptide, or a polynucleotide sequence encoding the adropin polypeptide.

In some embodiments, the probe is an antibody. In some embodiments, the probe is a polynucleotide complementary to the polynucleotide sequence encoding the adropin polypeptide. In some embodiments, the polynucleotide probe hybridizes to the polynucleotide sequence encoding the adropin polypeptide.

In some embodiments, the probe comprises a detection signal moiety. In some embodiments, the signal moiety generates a chemically and/or a physically detectable reaction.

In some embodiments, the kit comprises instructions for: contacting a sample of the subject with the molecular probe; detecting the adropin polypeptide, or a polynucleotide sequence encoding the adropin polypeptide in the sample; and determining the expression level of the adropin polypeptide, or a polynucleotide sequence encoding the adropin polypeptide in the sample compared to the control sample.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 8A-8C are vertical bar graphs showing that the inhibitory effect of adropin on MC-38 cells (colorectal cancer cell line) depends on seeded cells concentration (using XTT assay). No significant reduction was observed for adropin (25 or 100 ng/ml) when supplemented to MC-38 cells seeded at a density of (A) $5 \times 10^4$ (cells/well). A significant reduction in cell number was observed when 100 ng/ml of adropin was supplemented to (B) $5 \times 10^3$ (cells/well) or (C) $1 \times 10^3$ (cells/well). p<0.01, *p<0.0001.

FIGS. 9A-9D are vertical bar graphs showing the inhibitory effect of adropin on colorectal cancer cells. XTT metabolic assays showed significant inhibition of adropin on proliferation of MC38 (A) and CT26 (C) colorectal cancer cell lines, seeded at a concentration of $5 \times 10^3$ cells/well. The same trends of inhibition were demonstrated using direct cell counts for the MC38 (B) and CT26 (D) cells. *p<0.1, p<0.01, *p<0.0001.

FIGS. 10A-10C are vertical bar graphs showing the specificity of adropin inhibition on proliferating cancer cells. No detectable effect of adropin treatment was observed (using XTT assay) on normal (A) fibroblasts ($1 \times 10^4$ HF cells/well), (B) kidney cells ($5 \times 10^4$ cells/well), and (C) hepatocytes ($5 \times 10^4$ HepRG cells/well) in-vitro.

FIG. 11 is a graph showing adropin dynamic stability during incubation with mouse serum as measured with liquid chromatography mass spectrometry (LC-MS).

FIGS. 12A-12B are vertical bar graphs showing the effect of single adropin polypeptide injection on endogenous hepatic adropin RNA (A) and (B) protein levels at the indicated doses and timing following i.p. injection (n represents number of mice per group).

FIGS. 13A-13B are vertical bar graphs showing the dose effects of adropin treatment on the average number of metastases/total size (A) and average % growth/total liver size (B) of colorectal liver metastases (CRLM) development in C57BL/6 mice in vivo (n represents number of mice per group).

DETAILED DESCRIPTION OF THE INVENTION

Figure 1:
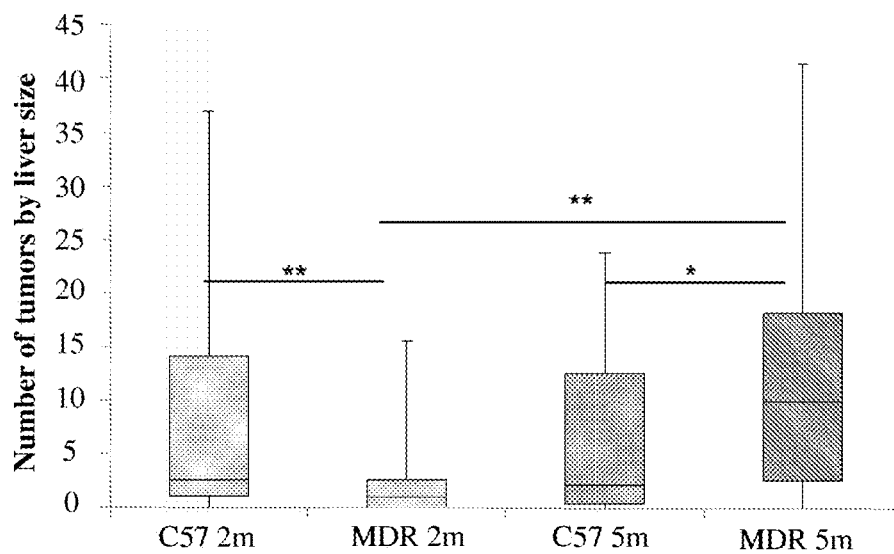
FIG. 1 is a bar graph depicting the relative number of metastases normalized to liver size by strain (i.e., C57 and MDR) and age (i.e., 2 months (2 m) and 5 m; n=10 mice/group; **p<0.01).

The present invention, in some embodiments thereof, is directed to methods for treating and/or preventing cancer, including but not limited to liver metastases, comprising pharmaceutical compositions comprising adropin. Further, the present invention, in some embodiments thereof, is directed to a method for diagnosing and/or prognosing liver metastases by determining adropin expression levels.

The present invention is based, in part, on the finding of a negative correlation between the levels of hepatic adropin and hepatic metastases (number and size). As demonstrated herein below, increased number and size of liver metastases coincided with low levels of hepatic adropin.

The invention is further based, in part, on the finding that by increasing the endogenous adropin levels, a reduction in liver metastases number and size is achieved (i.e., a response relevant for cancer therapy). As exemplified herein, administration of an adropin stimulating agent, e.g., adropin polypeptide, increased the endogenous hepatic adropin production (RNA and protein levels).

Adropin Stimulating Agent

As used herein, the term "adropin stimulating agent" refers to a molecule having a specific activity of increasing the expression of an endogenous adropin.

As used herein, the term "endogenous adropin" refers to the adropin gene or protein of a subject being elevated or increased by administration of the adropin stimulating agent of the invention.

In some embodiments, the adropin stimulating agent comprises a polypeptide comprising an amino acid sequence, having at least 80% homology to SEQ ID NO: 1, (CHSRSADVDSLSESSPNS SPGPCPEKAPPPQKP-SHEGSYLLQP). In some embodiments, at least 80% comprises: at least 85% homology, at least 90% homology, at least 95% homology, or 100% homology to SEQ ID NO: 1. Each possibility represents a separate embodiment of the present invention.

In some embodiments, the adropin stimulating agent is a human adropin. As used herein, human adropin has the amino acid sequence as set forth under UniProt accession no. Q6UWT2, wherein both Q6UWT2-1 (SEQ ID NO: 1) and Q6UWT2-2 (CHSRSADVDSLSESRTQESACLELD-PAAQSLASLAPIGAQWP) (SEQ ID NO: 2) isoforms are contemplated.

In some embodiments, the adropin stimulating agent comprises a polynucleotide comprising a sequence encoding an adropin polypeptide. In some embodiments, the polynucleotide comprising a sequence encoding an adropin polypeptide encodes for SEQ ID NO: 1. In some embodiments, the polynucleotide comprising a sequence encoding an adropin polypeptide encodes for a polypeptide having at least 80% homology to SEQ ID NO: 1.

As used herein, the terms "peptide", "polypeptide" and "protein" are interchangeable and refer to a polymer of amino acid residues. As used herein, the term "peptide", encompasses a native peptide, a peptidomimetic (typically including non-peptide bonds or other synthetic modifications), a peptide analog, peptoid, semi-peptoid, or any combination thereof. In another embodiment, the term "peptide", applies to an amino-acids polymer in which one or more amino acid residues is an artificial chemical analog of a corresponding naturally occurring amino acid.

As used herein, the term "derived from" or "corresponding to" refers to construction of an amino acid sequence based on the knowledge of a sequence using any one of the suitable means known to one skilled in the art, e.g., chemical synthesis in accordance with standard protocols in the art.

One of skill in the art will recognize that individual substitutions, deletions or additions to a peptide, or protein sequence which alters, adds or deletes a single amino acid or a small percentage of amino acids in the encoded sequence is a conservatively modified variant where the alteration results in the substitution of an amino acid with a similar charge, size, and/or hydrophobicity characteristics, such as, for example, substitution of a glutamic acid (E) to aspartic acid (D).

In some embodiments, the polypeptide described herein comprising a sequence having greater than 70%, 75%, 80%, 85%, 90%, 91%, 92%, 93%, 94%, 95%, 96%, 97%, 98%, or 99% homology to SEQ ID NO: 1 is considered an adropin stimulating agent as long as it shows substantially similar therapeutic activity as SEQ ID NO: 1. In some embodiments, SEQ ID NO: 1 therapeutic activity comprises one or more effects selected from the group consisting of: increasing endogenous adropin RNA levels, increasing endogenous adropin protein production levels, increasing endogenous adropin protein secretion levels, decreasing metastases number, and decreasing metastases size.

As used herein, the term "analog" includes any peptide having an amino acid sequence substantially identical to one of the sequences specifically shown herein in which one or more residues have been conservatively substituted with a functionally similar residue and which displays the abilities or activities as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. Each possibility represents a separate embodiment of the present invention.

As used herein, the phrase "conservative substitution" also includes the use of a chemically derivatized residue in place of a non-derivatized residue provided that such peptide displays the requisite function as specified herein.

In another embodiment, the term "variant" refers to a polypeptide or nucleotide sequence which comprises a modification of one or more amino acids or nucleotides as compared to another polypeptide or polynucleotide, respectively. In some embodiments, the modification is a substitution, a deletion, and/or an insertion of one or more amino acids or nucleotides as compared to another polypeptide or polynucleotide, respectively. In some embodiments, the changes may be of minor nature, such as conservative amino acid substitutions or for nucleotide sequence resulting in conservative amino acid substitutions that do not significantly affect the activity of the polypeptide. In some embodiments, the changes may be substitution of an amino acid molecule, resulting in an addition of a glycosylation site, thereby increasing glycosylation of the polypeptide.

In some embodiments, the invention encompasses derivatives of an adropin polypeptide. The term "derivative" or "chemical derivative" includes any chemical derivative of the polypeptide having one or more residues chemically derivatized by reaction of side chains or functional groups, which displays the abilities or activities as described herein. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides, which contain one or more naturally occurring amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted or serine; and ornithine may be substituted for lysine.

In addition, a polypeptide derivative can differ from the natural sequence of the adropin polypeptide of the invention (e.g., SEQ ID NO: 1) by chemical modifications including, but are not limited to, terminal-NH2 acylation, acetylation, or thioglycolic acid amidation, and by terminal-carboxylyamidation, e.g., with ammonia, methylamine, and the like, as long as the derivative molecule maintains the adropin stimulating activity. Peptides can be either linear, cyclic or branched and the like, which conformations can be achieved using methods well known in the art.

The polypeptide derivatives and analogs according to the principles of the present invention can also include side chain bond modifications, including but not limited to —CH2-NH—, —CH2-S—, —CH2-S=O, OC—NH—, —CH2-O—, —CH2-CH2-, S=C—NH—, and —CH=CH—, and backbone modifications such as modified peptide bonds. Peptide bonds (—CO—NH—) within the polypeptide can be substituted, for example, by N-methylated bonds (—N(CH3)—CO—); ester bonds (—C(R)H—C—O—O—C(R)H—N); ketomethylene bonds (—CO—CH2-); a-aza bonds (—NH—N(R)—CO—), wherein R is any alkyl group, e.g., methyl; carba bonds (—CH2-NH—); hydroxyethylene bonds (—CH(OH)—CH2-); thioamide bonds (—CS—NH); olefmic double bonds (—CH=CH—); and peptide derivatives (—N(R)—CH2-CO—), wherein R is the "normal" side chain, naturally presented on the carbon atom. These modifications can occur at one or more of the bonds along the peptide chain and even at several (e.g., 2-3) at the same time.

The polypeptide analogs can also contain non-natural amino acids. Examples of non-natural amino acids include, but are not limited to, sarcosine (Sar), norleucine, ornithine, citrulline, diaminobutyric acid, homoserine, isopropyl Lys, 3-(2'-naphtyl)-Ala, nicotinyl Lys, amino isobutyric acid, and 3-(3'-pyridyl-Ala).

Furthermore, the polypeptide analogs can contain other derivatized amino acid residues including, but not limited to, methylated amino acids, N-benzylated amino acids, O-benzylated amino acids, N-acetylated amino acids, O-acetylated amino acids, carbobenzoxy-substituted amino acids and the like. Specific examples include, but are not limited to, methyl- Ala (Me Ala), MeTyr, MeArg, MeGlu, MeVal, MeHis, N-acetyl-Lys, O-acetyl-Lys, carbobenzoxy-Lys, Tyr-O-Benzyl, Glu-O-Benzyl, Benzyl-His, Arg-Tosyl, t-butylglycine, t-butylalanine, phenylglycine, cyclohexylalanine, and the like.

The invention further encompasses polypeptide analogs, which can contain one or more D-isomer forms of the amino acids. Production of retro-inverso D-amino acid peptides where at least one amino acid and perhaps all amino acids are D-amino acids is well known in the art. When all of the amino acids in the peptide are D-amino acids, and the N- and C-terminals of the molecule are reversed, the result is a molecule having the same structural groups being at the same positions as in the L-amino acid form of the molecule. However, the molecule is more stable to proteolytic degradation and is therefore useful in many of the applications recited herein. Diastereomeric peptides may be highly advantageous over all L- or all D-amino acid peptides having the same amino acid sequence because of their higher water solubility, lower immunogenicity, and lower susceptibility to proteolytic degradation. The term "diastereomeric peptide" as used herein refers to a peptide comprising both L-amino acid residues and D-amino acid residues. The number and position of D-amino acid residues in a diastereomeric peptide of the preset invention may be variable so long as the peptide is capable of displaying the function of the disclosed polypeptide of the invention, e.g., treating or reducing liver metastases.

Included within the scope of the invention are peptide conjugates (interchangeably "fusion proteins") comprising the peptide of the present invention derivatives, or analogs thereof joined at their amino or carboxy-terminus or at one of the side chains, such as via a peptide bond, to an amino acid sequence corresponding to or derived from a different protein.

Non-limiting examples of fusion proteins of the invention exhibit a longer serum half-life while maintaining therapeutic effect, relative to the corresponding human adropin.

In some embodiments, the term "serum half-life" refers to the time it takes for a substance to lose half of its pharmacologic, physiologic, or radiologic activity following introduction of an amount of the substance into the serum of an organism. In another embodiment, serum half-life refers to the time it takes for a substance to be reduced to half of a starting amount introduced into the serum of an organism, following such introduction. In some embodiments, an adropin polypeptide has a substantially increased serum half-life, e.g., from minutes to several days. Biological stability (or serum half-life) can be measured by a variety of in vitro or in vivo means. For example, differences in half-life can be compared by using a radiolabeled version of each protein to be compared and measuring levels of serum radioactivity as a function of time in the same or different organism. Additionally, serum half-life can be compared by assaying the levels of exogenous human adropin present in serum using ELISA as a function of time in the same or different organism.

In some embodiments, a conjugate comprising the adropin polypeptide of the invention and a protein can be made by protein synthesis, e.g., by use of a peptide synthesizer, or by ligating the appropriate nucleic acid sequences encoding the desired amino acid sequences to each other by methods known in the art, in the proper coding frame, and expressing the conjugate by methods commonly known in the art.

Addition of amino acid residues may be performed at either terminus of the adropin polypeptide of the invention for the purpose of providing a "linker" by which the polypeptides of this invention can be conveniently bound to a carrier. Such linkers are usually of at least one amino acid residue and can be of 40 or more residues, more often of 1 to 10 residues. Typical amino acid residues used for linking are tyrosine, cysteine, lysine, glutamic and aspartic acid, or the like.

The adropin polypeptide of the invention may be synthesized or prepared by techniques well known in the art. The polypeptide can be synthesized by a solid phase peptide synthesis method of Merrifield (see J. Am. Chem. Soc, 85:2149, 1964). Alternatively, the adropin polypeptide can be synthesized using standard solution methods well known in the art (see, for example, Bodanszky, M., Principles of Peptide Synthesis, Springer-Verlag, 1984) or by any other method known in the art for peptide synthesis.

As used herein, the term "adropin stimulating agent" comprises a polynucleotide (e.g., DNA or RNA) sequence that comprises coding sequences necessary for the production of an adropin prolylpeptide. In one embodiment, a polynucleotide refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein, the term "complementary polynucleotide sequence" refers to a sequence, which results from reverse transcription of messenger RNA using a reverse transcriptase or any other RNA dependent DNA polymerase. In one embodiment, the sequence can be subsequently amplified in vivo or in vitro using a DNA polymerase.

As used herein, the term "genomic polynucleotide sequence" refers to a sequence derived (isolated) from a chromosome and thus it represents a contiguous portion of a chromosome.

As used herein, the term "composite polynucleotide sequence" refers to a sequence, which is at least partially complementary and at least partially genomic. In one embodiment, a composite sequence can include some exonal sequences required to encode the adropin polypeptide of the present invention, as well as some intronic sequences interposing there between. In one embodiment, the intronic sequences can be of any source, including of other genes, and typically will include conserved splicing signal sequences. In one embodiment, intronic sequences include cis acting expression regulatory elements.

In some embodiments, a polynucleotide encoding an adropin polypeptide comprises a polynucleotide sequence encoding any one of the polypeptides of the invention. In another embodiment, the polynucleotide encoding an adropin polypeptide is at least 60%, at least 65%, at least 70%, at least 80%, at least 90%, at least 95%, or at least 99% homologous to the polynucleotide encoding the adropin polypeptide of the invention (SEQ ID NO: 1) or a derivative thereof.

In some embodiments, a polynucleotide encoding an adropin polypeptide of the present invention is ligated into an expression vector, comprising a transcriptional control of a cis-regulatory sequence (e.g., promoter sequence). In some embodiments, the cis-regulatory sequence is suitable for directing constitutive expression of the adropin polypeptide of the present invention. In some embodiments, the cis-regulatory sequence is suitable for directing tissue-specific expression of the polypeptide of the present invention. In some embodiments, the cis-regulatory sequence is suitable for directing inducible expression of the polypeptide of the present invention.

In some embodiments, the polynucleotide encoding the adropin polypeptide of the present invention is prepared using polymerase chain reaction (PCR) techniques, or any other method or procedure known to one skilled in the art.

In one embodiment, the polynucleotide encoding the adropin polypeptide is inserted into expression vectors (i.e., a nucleic acid construct) to enable expression of a recombinant adropin polypeptide. In one embodiment, the expression vector includes additional sequences which render this vector suitable for replication and integration in prokaryotes. In one embodiment, the expression vector includes additional sequences which render this vector suitable for replication and integration in eukaryotes. In one embodiment, the expression vector includes a shuttle vector which renders this vector suitable for replication and integration in both prokaryotes and eukaryotes. In some embodiments, cloning vectors comprise transcription and translation initiation sequences (e.g., promoters, enhancers) and transcription and translation terminators (e.g., polyadenylation signals).

In one embodiment, a variety of prokaryotic or eukaryotic cells can be used as host-expression systems to express the adropin polypeptide of the present invention. In some embodiments, these include, but are not limited to, microorganisms, such as bacteria transformed with a recombinant bacteriophage DNA, plasmid DNA or cosmid DNA expression vector containing the polynucleotide sequence encoding the adropin polypeptide or the adropin polypeptide coding sequence; yeast transformed with recombinant yeast expression vectors containing the polynucleotide sequence encoding the adropin polypeptide or the adropin polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polynucleotide sequence encoding the adropin polypeptide or the adropin polypeptide coding sequence.

In some embodiments, non-bacterial expression systems are used (e.g. mammalian expression systems) to express the adropin polypeptide of the present invention. In one embodiment, the expression vector is used to express the polynucleotide encoding the adropin polypeptide of the present invention in mammalian cells.

In some embodiments, in bacterial systems, a number of expression vectors can be advantageously selected depending upon the use intended for the polypeptide expressed. In one embodiment, large quantities of polypeptide are desired. In one embodiment, vectors that direct the expression of high levels of the protein product, possibly as a fusion with a hydrophobic signal sequence, which directs the expressed product into the periplasm of the bacteria or the culture medium where the protein product is readily purified are desired. In one embodiment, certain fusion protein engineered with a specific cleavage site to aid in recovery of the polypeptide. In one embodiment, vectors adaptable to such manipulation include, but are not limited to, the pET series of E. coli expression vectors [Studier et al., Methods in Enzymol. 185:60-89 (1990)].

In one embodiment, yeast expression systems are used. In one embodiment, a number of vectors containing constitutive or inducible promoters can be used in yeast as disclosed in U.S. Pat. No. 5,932,447. In another embodiment, vectors which promote integration of foreign DNA sequences into the yeast chromosome are used.

In one embodiment, the expression vector may further include additional polynucleotide sequences that allow, for example, the translation of several proteins from a single mRNA such as an internal ribosome entry site (IRES).

In some embodiments, mammalian expression vectors include, but are not limited to, pcDNA3, pcDNA3.1 (±), pGL3, pZeoSV2(±), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

In some embodiments, expression vectors containing regulatory elements from eukaryotic viruses such as retroviruses are used by the present invention. SV40 vectors include pSVT7 and pMT2. In some embodiments, vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In some embodiments, recombinant viral vectors, which offer advantages such as lateral infection and targeting specificity, are used for in vivo expression of the adropin polypeptide of the present invention. In one embodiment, lateral infection is inherent in the life cycle of, for example, retrovirus and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

Various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In one embodiment, plant expression vectors are used. In one embodiment, the expression of a polypeptide coding sequence is driven by a number of promoters. In some embodiments, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the adropin polypeptide), the expression construct can also include sequences engineered to optimize stability, production, purification, yield or activity of the expressed polypeptide.

In some embodiments, transformed cells are cultured under effective conditions, which allow for the expression of high amounts of a recombinant polypeptide. In some embodiments, effective culture conditions include, but are not limited to, effective media, bioreactor, temperature, pH and oxygen conditions that permit protein production. In one embodiment, an effective medium refers to any medium in which a cell is cultured to produce a recombinant adropin polypeptide of the present invention. In some embodiments, a medium typically includes an aqueous solution having assimilable carbon, nitrogen and phosphate sources, and appropriate salts, minerals, metals and other nutrients, such as vitamins. In some embodiments, the cells can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, culturing conditions are within the expertise of one of ordinary skill in the art.

In some embodiments, depending on the vector and host system used for production, resultant adropin polypeptide of the present invention either remains within the recombinant cell, secreted into the fermentation medium, secreted into a space between two cellular membranes, such as the periplasmic space in E. coli; or retained on the outer surface of a cell or viral membrane. In one embodiment, following a predetermined time in culture, recovery of the recombinant polypeptide is affected.

In one embodiment, the phrase "recovering the recombinant polypeptide" used herein refers to collecting the whole fermentation medium containing the polypeptide and need not imply additional steps of separation or purification.

In one embodiment, an adropin polypeptide of the present invention is purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In one embodiment, to facilitate recovery, the expressed coding sequence can be engineered to encode the adropin polypeptide of the present invention and fused cleavable moiety. In one embodiment, a fusion protein can be designed so that the polypeptide can be readily isolated by affinity chromatography; e.g., by immobilization on a column specific for the cleavable moiety. In one embodiment, a cleavage site is engineered between the polypeptide and the cleavable moiety, and the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265: 15854-15859 (1990)].

In one embodiment, the adropin polypeptide of the present invention is retrieved in "substantially pure" form that allows for the effective use of the protein in the applications described herein.

As used herein, the term "substantially pure" describes a peptide/polypeptide or other material which has been separated from its native contaminants. Typically, a monomeric peptide is substantially pure when at least about 60 to 75% of a sample exhibits a single peptide backbone. Minor variants or chemical modifications typically share the same peptide sequence. A substantially pure peptide can comprise over about 85 to 90% of a peptide sample, and can be over 95% pure, over 97% pure, or over about 99% pure. Purity can be measured on a polyacrylamide gel, with homogeneity determined by staining. Alternatively, for certain purposes high resolution may be necessary and HPLC or a similar means for purification can be used. For most purposes, a simple chromatography column or polyacrylamide gel can be used to determine purity.

The term "purified" does not require the material to be present in a form exhibiting absolute purity, exclusive of the presence of other compounds. Rather, it is a relative definition. A peptide is in the "purified" state after purification of the starting material or of the natural material by at least one order of magnitude, 2 or 3, or 4 or 5 orders of magnitude.

In one embodiment, the adropin polypeptide of the present invention is substantially free of naturally-associated host cell components. The term "substantially free of naturally-associated host cell components" describes a peptide or other material which is separated from the native contaminants which accompany it in its natural host cell state. Thus, a peptide which is chemically synthesized or synthesized in a cellular system different from the host cell from which it naturally originates will be free from its naturally-associated host cell components.

In one embodiment, the adropin polypeptide of the present invention can also be synthesized using in vitro expression systems. In one embodiment, in vitro synthesis methods are well known in the art and the components of the system are commercially available. Non-limited example for in vitro system includes, but is not limited to, in vitro translation.

In some embodiments, an adropin stimulating agent can be selected from the group consisting of: a carbohydrate, a lipid, a small organic molecule and an inorganic molecule.

Methods of Treatment

In some embodiments, the present invention is directed to a method for treating or preventing cancer in a subject in need thereof, comprising administering to the subject a therapeutically effective amount of an adropin stimulating agent.

As used herein, the term "cancer" refers to diseases associated with cell proliferation.

In some embodiments, the subject is suspected to develop cancer. In some embodiments, the subject is suspected to develop a secondary cancer. In some embodiments, the subject is suspected to develop liver metastases. In some embodiments, the subject is at risk of developing cancer.

As defined herein, the term "metastasis" refers to a secondary malignant growth located distantly from the primary cancerous site.

In some embodiments, the method further comprises the step of identifying a subject suspected to develop cancer. In some embodiments, the method further comprises the step of identifying a subject suspected to develop a secondary cancer. In some embodiments, the method further comprises the step of identifying a subject suspected to develop liver metastases.

In some embodiments, the present invention is directed to a method for preventing cancer dissemination in a subject, comprising the step of administering to the subject a therapeutically effective amount of an adropin stimulating agent (polypeptide of the invention or derivative thereof or a polynucleotide encoding thereof).

Non-limiting examples of desirable effects demonstrating cancer dissemination prevention include, but are not limited to, reduced probability of being afflicted with cancer, reduced probability of cancer metastases formation, or both.

In some embodiments, the method is directed to decrease tumor size, decrease metastases frequency, or a combination thereof.

In some embodiments, the method further comprises monitoring one or more symptoms selected from, without being limited thereto, growth or angiogenesis of a metastatic tumor, presence of circulating tumor cells, and appearance of a new metastasis.

In some embodiments, the method further comprises monitoring the effect of adropin levels on one or more symptoms selected from, without being limited thereto, growth or angiogenesis of a metastatic tumor, presence of circulating tumor cells, and appearance of a new metastasis.

In some embodiments, the monitoring further comprises determining cancer or metastasis progression. In some embodiments, determining cancer or metastasis progression is by detecting a symptom selected from, without being limited thereto, tumor size, tumor growth, number of metastases, size of metastases, number of circulating tumor cells in blood, vascularization in tissue adjacent to the tumors, adropin RNA levels, adropin protein production levels, and adropin secretion levels.

In some embodiments, the cancer is a secondary, i.e., a metastatic cancer. In some embodiments, the secondary cancer is in an adropin-expressing organ. In some embodiments, the adropin-expressing organ metastatic cancer is a liver metastasis. In some embodiments, the adropin-expressing organ metastatic cancer is a brain metastasis.

In one embodiment, the cancer is other than a gynecologic cancer. In another embodiment, the cancer is other than endometrium cancer. In another embodiment, the subject being treated does not suffer from a metabolic syndrome or disorder including but not limited to obesity, insulin resistance or impaired glucose tolerance or hemostasis.

In some embodiments, the metastases (e.g., liver metastases) is sourced from a primary cancer selected from, without being limited thereto, colorectal, lung, breast, pancreatic, stomach, melanoma, neuroendocrine, and esophageal cancer.

In some embodiments, the method further comprises administering to the subject a therapeutically effective amount of polynucleotide construct comprising an NRP2-gene silencing sequence. In some embodiments, the method further comprises administering to the subject a therapeutically effective amount of a polynucleotide construct comprising an NRP2 inhibitor. The Entrez Gene ID and the UnipProt accession no. of human NRP2 is 8828, and 060462, respectively. One skilled in the art is capable of determining and providing an NRP2-gene silencing sequence or an NRP2 inhibitor. Non-limiting examples for methods of NRP2 gene silencing include, but are not limited to, RNA interference, knock-out, knock-in, knock-down, or any other method known in the art of functional genomics.

As used herein, the term "subject" refers to an animal, more particularly to non-human mammals and human organism. Non-human animal subjects may also include prenatal forms of animals, such as, e.g., embryos or fetuses. Non-limiting examples of non-human animals include: horse, cow, camel, goat, sheep, dog, cat, non-human primate, mouse, rat, rabbit, hamster, guinea pig, pig. In one embodiment, the subject is a human. Human subjects may also include fetuses. In one embodiment, a subject in need thereof is a subject afflicted with and/or at risk of being afflicted with a condition associated with increased cell proliferation.

As used herein, the terms "treatment" or "treating" of a disease, disorder, or condition encompasses alleviation of at least one symptom thereof, a reduction in the severity thereof, or inhibition of the progression thereof. Treatment need not mean that the disease, disorder, or condition is totally cured. To be an effective treatment, a useful composition herein needs only to reduce the severity of a disease, disorder, or condition, reduce the severity of symptoms associated therewith, or provide improvement to a patient or subject's quality of life.

As used herein, the terms "preventing", or "prevention" of a disease, disorder, or condition encompasses the delay, prevention, suppression, inhibition of the onset of a disease, disorder, or condition or reducing the probability of onset of the disease/disorder process. As used in accordance with the presently described subject matter, the term "prevention" relates to a process of prophylaxis in which a subject is exposed to the presently described adropin polypeptide or a polynucleotide encoding thereof prior to the induction or onset of the disease/disorder process. This could be done where an individual has a genetic pedigree indicating a predisposition toward occurrence of the disease/disorder to be prevented. For example, this might be true of an individual whose ancestors show a predisposition toward certain types of, for example, inflammatory disorders. The term "suppression" is used to describe a condition wherein the disease/disorder process has already begun but obvious symptoms of the condition have yet to be realized. Thus, the cells of an individual may have the disease/disorder, but no outside signs of the disease/disorder have yet been clinically recognized. In either case, the term prophylaxis can be applied to encompass both prevention and suppression. Conversely, the term "treatment" refers to the clinical application of active agents to combat an already existing condition whose clinical presentation has already been realized in a patient.

As used herein, the term "condition" includes anatomic and physiological deviations from the normal that constitute an impairment of the normal state of the living animal or one of its parts, that interrupts or modifies the performance of the bodily functions.

Method of Increasing Adropin Expression

In some embodiments, there is provided a pharmaceutical composition comprising a low dose of adropin. In some embodiments, the pharmaceutical composition is used to induce an increase in hepatic adropin expression level. In some embodiments, the pharmaceutical composition is effective in inducing an increase in hepatic adropin expression level.

In some embodiments, the present invention is directed to a method for increasing adropin expression. In some embodiments, the method is for increasing hepatic adropin expression. In some embodiments, the method results in increased hepatic adropin expression levels. In some embodiments, there is provided a method for inducing increase in hepatic adropin expression levels. In some embodiments, there is provided a method for promoting increase in hepatic adropin expression levels.

In some embodiments, a method for inducing hepatic adropin expression comprises administering to a subject in need thereof a pharmaceutical composition comprising low dose of the adropin.

As used herein, the terms "low dose" or "lower dose" are in comparison to the dose used or known such as in the context of metabolic disease(s). As used herein, an adropin polypeptide used for treating or preventing a metabolic disease is considered being a "high dose" or a "higher dose". In some embodiments, an adropin polypeptide is administered or used in a higher dose to treat metabolic disease(s) compared to the lower dose of an adropin polypeptide administered to induce increase in hepatic adropin expression.

As used herein, a low dose of adropin is 2-fold less, 3-fold less, 4-fold less, 5-fold less, 6-fold less, 7-fold less, 8-fold less, 9-fold less, 10-fold less, 20-fold less, 30-fold less, 40-fold less, or 50-fold less than high dose, including any value or range therebetween. In some embodiments, a low dose is 5-15% less, 10-30% less, 25-40% less, 35-50% less, 40-65% less, 55-75% less, 70-90% less, or 85-100% less than a high dose, including any value or range therebetween. In some embodiments, a low dose is at least 5%, at least 10%, at least 20%, at least 35% at least 45%, at least 55%, at least 65%, at least 75%, at least 85%, at least 95%, or at least 99% less than a high dose, including any value or range therebetween. Each possibility represents a separate embodiment of the present invention.

In some embodiments, the adropin polypeptide is administered in a dose range of 1 to 100 nmole/kg human body. In some embodiments, the adropin polypeptide is administered in a dose of 1, 2, 3, 4, 5, 6, 7, 8, 9, and 10 nmol/kg human body, including any value and range therebetween. In some embodiments, the adropin polypeptide is administered in a dose of 1, 10, 20, 30, 40, 50, 60, 70, 80, 90, and 100 nmole/kg human body, including any value and range therebetween. In some embodiments, the adropin polypeptide is administered in a dose of 20, 22, 24, 26, 28, 30, 32, 34, 36, 38, 40, 42, 44, 46, 48, and 50 nmole/kg human body, including any value and range therebetween. In some embodiments, the adropin polypeptide is administered in a dose of 30, 31, 32, 33, 34, 35, 36, 37, 38, 39, 40, 41, and 42 nmole/kg human body, including any value and range therebetween. In some embodiments, the adropin polypeptide is administered in a dose of 35, 35.1, 35.2, 35.3, 35.4, 35.5, 35.6, 35.7, 35.8, 35.9, 36, 36.1, 36.2, 36.3, 36.4, 36.5, 36.6, 36.7, 36.8, 36.9, 37, 37.1, 37.2, 37.3, 37.4, 37.5, 37.6, 37.7, 37.8, 37.9, and 38 nmole/kg human body, including any value and range therebetween. Each value represents a separate embodiment of the present invention.

In some embodiments, the present invention is directed to a pharmaceutical composition comprising the adropin polypeptide in a unit dose.

As used herein, a "unit dose" is a discrete amount of the pharmaceutical composition comprising a predetermined amount of the active ingredient (e.g., the adropin polypeptide). The amount of the active ingredient is generally equal to the dosage of the active ingredient which would be administered to a subject and/or a convenient fraction of such a dosage such as, for example, one-half or one-third of such a dose.

As used herein, a unit dose comprises the low dose as described hereinabove. In some embodiments, the amount of the adropin polypeptide in a unit dose ranges between 0.003 mg to 0.1 mg. In some embodiments, the amount of the adropin polypeptide in a unit dose is 0.001 mg, 0.002 mg, 0.003 mg, 0.004 mg, 0.005 mg, 0.006 mg, 0.007 mg, 0.008 mg, 0.009 mg, or 0.01 mg, including any value and range therebetween. In some embodiments, the amount of the adropin polypeptide in a unit dose is 0.01 mg, 0.02 mg, 0.03 mg, 0.04 mg, 0.05 mg, 0.06 mg, 0.07 mg, 0.08 mg, 0.09 mg, or 0.1 mg, including any value and range therebetween.

Methods of Diagnosis

In some embodiments, the present invention is directed to a method of diagnosing a tendency for metastatic cancer dissemination to the liver in a subject in need thereof, comprising the steps of: obtaining a sample from the subject, and determining the level of adropin in the sample, wherein reduced level of adropin in the sample compared to control sample is indicative of predisposition to liver metastases in the subject.

In some embodiments, the present invention is directed to a method of prognosing liver metastases in a subject, comprising: obtaining a sample from the subject, and determining the level of adropin in the sample, wherein reduced levels of adropin in the sample compared to control sample is indicative of the severity of liver metastases in the subject.

In some embodiments, "reduced" or "reduction" comprises a decreased level of at least 5%, at least 20%, at least 35%, at least 50%, at least 75%, at least 85%, at least 90%, at least 95%, or at least 100% compared to control. In some embodiments, "reduced" or "reduction" comprises a decreased level of 5-15%, 10-20%, 17-35%, 30-50%, 40-75%, 60-85%, 70-90%, 80-95%, or 85-100% compared to control. In some embodiments, "reduced" or "reduction" comprises a decreased level of at least 2-fold, at least 5-fold, at least 10-fold, at least 20-fold, at least 50-fold, at least 100-fold, at least 500-fold, or at least 1,000-fold compared to control. In some embodiments, "reduced" or "reduction" comprises a decreased level of 2-5-fold, 4-20-fold, 17-50-fold, 30-100-fold, 75-250-fold, 200-500-fold, or 400-1,200-fold compared to control. Each possibility represents a separate embodiment of the present invention.

In some embodiments, the adropin level within the sample negatively correlates with the number and/or size of liver metastases. As exemplified herein, when the adropin level is high the number and/or size of liver metastases is low. Alternatively, it is exemplified herein that when the adropin level is low the number and/or size of liver metastases is increased.

In some embodiments, the sample comprises any tissue or cells obtained from the subject or a body fluid thereof. In some embodiments, the sample is selected from, without being limited thereto, a liver sample or a bodily fluid, such as a blood sample.

In some embodiments, the control sample is a tissue of a non-afflicted subject. In some embodiments, the control sample is a body fluid of a non-afflicted subject. In some embodiments, the control sample is a benign tissue of an afflicted subject. In some embodiments, the control sample is a tumor neighboring or adjacent tissue of an afflicted subject. In some embodiments, the control sample is a tissue collected from the subject at a time the subject was determined or diagnosed as cancer-free.

In some embodiments, the determination of adropin level is performed via evaluating the adropin protein production levels, the adropin secretion levels, or both.

In some embodiments, the evaluation of the adropin protein production levels, secretion levels, or both is established via an immunoassay. In some embodiments, the immunoassay is an enzyme-linked immunosorbent assay (ELISA).

In some embodiments, the determination of adropin level is performed via evaluating the expression level of the gene encoding the adropin. In some embodiments, the evaluation of the expression level of the gene encoding the adropin is established via determining the amount of RNA encoding adropin (Enho).

In one embodiment, adropin encoding sequence is amplified by means of DNA polymerase, such as in a polymerase chain reaction (PCR). DNA primers capable of amplifying the nucleic acid molecule can be designed by any known method in the art and would be apparent to one of ordinary skill in the art.

In one embodiment, PCR comprises denaturing double-stranded DNA in a sample (to separate the complementary strands), annealing the primers to the dissociated DNA strands, and extension reaction from the primers catalyzed by a thermostable DNA polymerase, the cycle is then repeated.

In one embodiment, methods for visualizing the nucleic acid molecule as described herein or the amplicons generated in the PCR is gel electrophoresis in polyacrylamide or agarose, followed by ethidium bromide staining. In some embodiments, a PCR amplicon is directly quantified in real-time of amplification, according to methods of real-time PCR or quantitative PCR, which would be apparent to a skilled artisan. The observed sizes of the amplified target fragment—the nucleic acid molecule as described herein, should be identical to the predicted from the known nucleotide sequence as described and exemplified. In one embodiment, methods for visualizing the nucleic acid molecule as described herein or the amplicons generated in the PCR comprises Southern blot probing, dot-blots, or any known DNA hybridization technique wherein the nucleic acid molecule as described herein is utilized as a probe. In some embodiments, a visualized nucleic acid can be quantified by densitometry, as would be apparent to one of ordinary skill in the art.

The term "probe" refers to a labeled or unlabeled oligonucleotide capable of selectively hybridizing to a target or template nucleic acid under suitable conditions. Typically, a probe is sufficiently complementary to a specific target sequence contained in a nucleic acid sample to form a stable hybridization duplex with the target sequence under a selected hybridization condition, such as, but not limited to, a stringent hybridization condition. A hybridization assay carried out using the probe under sufficiently stringent hybridization conditions permits the selective detection of a specific target sequence. For use in a hybridization assay for the discrimination of single nucleotide differences in sequence, the hybridizing region is typically from about 8 to about 100 nucleotides in length. Although the hybridizing region generally refers to the entire oligonucleotide, the probe may include additional nucleotide sequences that function, for example, as linker binding sites to provide a site for attaching the probe sequence to a solid support or the like, as sites for hybridization of other oligonucleotides, as restriction enzymes sites or binding sites for other nucleic acid binding enzymes, etc. In certain embodiments, a probe of the invention is included in a nucleic acid that comprises one or more labels (e.g., a reporter dye, a quencher moiety, a fluorescent labeling, etc.), such as a 5'-nuclease probe, a FRET probe, a molecular beacon, or the like, which can also be utilized to detect hybridization between the probe and target nucleic acids in a sample. In some embodiments, the hybridizing region of the probe is completely complementary to the target sequence. However, in general, complete complementarity is not necessary (i.e., nucleic acids can be partially complementary to one another); stable duplexes may contain mismatched bases or unmatched bases. Modification of the stringent conditions may be necessary to permit a stable hybridization duplex with one or more base pair mismatches or unmatched bases. Sambrook et al., Molecular Cloning: A Laboratory Manual, 3rd Ed., Cold Spring Harbor Laboratory Press, Cold Spring Harbor, N.Y. (2001), which is incorporated by reference, provides guidance for suitable modification. Stability of the target/probe duplex depends on a number of variables including length of the oligonucleotide, base composition and sequence of the oligonucleotide, temperature, and ionic conditions. One of skill in the art will recognize that, in general, the exact complement of a given probe is similarly useful as a probe. One of skill in the art will also recognize that, in certain embodiments, probe nucleic acids can also be used as primer nucleic acids. Exemplary probe nucleic acids include 5'-nuclease probes, molecular beacons, among many others known to persons of skill in the art.

In some embodiments, a probe utilized according to the method of the invention comprises DNA, RNA or LNA (locked nucleic acid) probe, or any combination thereof.

As used herein, "hybridization" refers to a reaction in which at least one polynucleotide reacts to form a complex that is stabilized via hydrogen bonding between the bases of the nucleotide residues. The hydrogen bonding may occur by. Watson-Crick base pairing, in any other sequence-specific manner. A hybridization reaction may constitute a step in a more extensive process, such as the initiation of a PCR reaction.

Hybridization reactions can be performed under conditions of different stringency. Under stringent conditions, nucleic acid molecules at least 60%, at least 65%, at least 70%, at least 75% identical to each other remain hybridized to each other. A non-limiting example of highly stringent hybridization conditions is hybridization in 6× Sodium chloride/Sodium citrate (SSC) at approximately 45° C., followed by one or more washes in 0.2×SSC and 0.1% SDS at 50° C., at 55° C., at 60° C., or more.

When hybridization occurs in an anti-parallel configuration between two single-stranded polynucleotides, those polynucleotides are described as complementary.

Hybridization based assays which allow the detection of a polynucleotide of interest in a biological sample rely on the use of probe(s) which can be 10, 15, 20, or 30 to 100 nucleotides long optionally from 10 to 50, or from 40 to 50 nucleotides long.

The detection of hybrid duplexes can be carried out by several methods. Typically, hybridization duplexes are separated from unhybridized nucleic acids and the labels bound to the duplexes are then detected. Such labels refer to radioactive, fluorescent, biological or enzymatic tags or labels of standard use in the art. A label can be conjugated to either the oligonucleotide probes or the nucleic acids derived from the biological sample.

Probes can be labeled according to numerous well-known methods. Non-limiting examples of detectable markers include ligands, fluorophores, chemiluminescent agents, enzymes, and antibodies. Other detectable markers for use with probes, which can enable an increase in sensitivity of the method of the invention, include biotin and radio-nucleotides. It will become evident to the person of ordinary skill that the choice of a particular label dictates the manner in which it is bound to the probe.

For example, oligonucleotides according to some embodiments of the present invention can be labeled subsequently to synthesis, by incorporating biotinylated dNTPs or rNTP, or some similar means (e.g., photo-cross-linking a psoralen derivative of biotin to RNAs), followed by addition of labeled streptavidin (e.g., phycoerythrin-conjugated streptavidin) or the equivalent. Alternatively, when fluorescently-labeled oligonucleotide probes are used, fluorescein, lissamine, phycoerythrin, rhodamine (Perkin Elmer Cetus), Cy2, Cy3, Cy3.5, Cy5, Cy5.5, Cy7, Fluor X (Amersham) and others (e.g., Kricka et al. (1992), Academic Press San Diego, Calif) can be attached to the oligonucleotides. Preferably, detection of the biomarkers of the invention is achieved by using TaqMan assays, preferably by using combined reporter and quencher molecules (Roche Molecular Systems Inc.).

Although the present invention is not specifically dependent on the use of a label for the detection of a particular nucleic acid sequence, such a label might be beneficial, by increasing the sensitivity of the detection. Furthermore, it enables automation. Probes can be labeled according to numerous well-known methods.

As commonly known, radioactive nucleotides can be incorporated into probes of the invention by several methods. Non-limiting examples of radioactive labels include $^3$H, $^{14}$C, $^{32}$P, and $^{35}$S.

Those skilled in the art will appreciate that wash steps may be employed to wash away excess target polynucleotide or probe as well as unbound conjugate. Further, standard heterogeneous assay formats are suitable for detecting the hybrids using the labels present on the oligonucleotide primers and probes.

It will be appreciated that a variety of controls may be usefully employed to improve accuracy of hybridization assays. For instance, samples may be hybridized to an irrelevant probe and treated with RNase A prior to hybridization, to assess false hybridization.

Probes according to a method of the invention can be utilized with naturally occurring sugar-phosphate backbones as well as modified backbones including phosphorothioates, dithionates, alkyl phosphonates and a-nucleotides and the like. Probes of the invention can be constructed of either ribonucleic acid (RNA) or deoxyribonucleic acid (DNA).

An additional nucleic acid test (NAT) test known in the art is fluorescence in situ hybridization (FISH). FISH is based on fluorescent single-stranded DNA or RNA probes which are complementary to the nucleotide sequences that are under examination (genes, chromosomes or RNA). These probes hybridize with the complementary nucleotide and allow the identification of the chromosomal location of genomic sequences of DNA or RNA.

Detection of a nucleic acid of interest in a biological sample may also optionally be affected by NAT-based assays, which involve nucleic acid amplification technology or assay, such as PCR for example (or variations thereof such as real-time PCR for example).

As used herein, the term "primer" refers to an oligonucleotide which is capable of annealing to (hybridizing with) a target sequence, thereby creating a double stranded region which can serve as an initiation point for DNA synthesis under suitable conditions. Although other primer nucleic acid lengths are optionally utilized, they typically comprise hybridizing regions that range from about 8 to about 100 nucleotides in length. Short primer nucleic acids generally utilize cooler temperatures to form sufficiently stable hybrid complexes with template nucleic acids. A primer nucleic acid that is at least partially complementary to a subsequence of a template nucleic acid is typically sufficient to hybridize with the template for extension to occur. A primer nucleic acid can be labeled (e.g., a SCORPION primer, etc.), if desired, by incorporating a label detectable by, e.g., spectroscopic, photochemical, biochemical, immunochemical, chemical, or other techniques. To illustrate, useful labels include radioisotopes, fluorescent dyes, electron-dense reagents, enzymes (as commonly used in ELISAs), biotin, or haptens and proteins for which antisera or monoclonal antibodies are available. Many of these and other labels are described further herein and/or otherwise known in the art. One of skill in the art will recognize that, in certain embodiments, primer nucleic acids can also be used as probe nucleic acids.

In some embodiments, the method further comprises the step of evaluating the expression level of the NRP2 gene. In some embodiments, the method further comprises the step of evaluating the NRP2 protein levels, as describe hereinabove. In some embodiments, the evaluation of the expression level of the NRP2 gene is established via determining the amount of the corresponding RNA transcript. In some embodiments, the prognosing further comprises correlating the NRP2 gene level with the number and size of metastases. In some embodiments, the correlating is a positive correlation.

Compositions

In some embodiments, the present invention is directed to a pharmaceutical composition comprising an adropin polypeptide comprising an amino acid sequence, having at least 80% homology to SEQ ID NO: 1, for use in treating cancer, such as liver metastases.

In some embodiments, the present invention is directed to a pharmaceutical composition comprising an adropin polynucleotide encoding the adropin polypeptide (SEQ ID NO: 1) or an adropin polypeptide having at least 80% homology to SEQ ID NO: 1, for use in treating cancer, such as liver metastases.

In another embodiment, the present invention is directed to a pharmaceutical composition further comprising a nucleic acid construct possessing a NRP2-gene silencing sequence.

In one embodiment, the present invention provides combined preparations. In one embodiment, "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

In one embodiment, it will be appreciated that the adropin stimulating agent of the present invention can be provided to the individual with additional active agents to achieve an improved therapeutic effect as compared to treatment with each agent by itself. In another embodiment, measures (e.g., dosing and selection of the complementary agent) are taken to adverse side effects which are associated with combination therapies.

In one embodiment, depending on the severity and responsiveness of the condition to be treated, dosing can be of a single or a plurality of administrations, with course of treatment lasting from several days to several weeks or until cure is affected or diminution of the disease state is achieved.

In some embodiments, the adropin stimulating agent is administered in a therapeutically safe and effective amount. As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the presently described manner. In another embodiment, a therapeutically effective amount of the adropin stimulating agent is the amount of the agent necessary for the in vivo measurable expected biological effect. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in Remington: The Science and Practice of Pharmacy, 21st Ed., Lippincott Williams & Wilkins, Philadelphia, Pa., (2005). In some embodiments, preparation of effective amount or dose can be estimated initially from in vitro assays. In one embodiment, a dose can be formulated in animal models and such information can be used to more accurately determine useful doses in humans.

In one embodiment, toxicity and therapeutic efficacy of the active ingredient (i.e., adropin stimulating agent) described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p.1].

Pharmaceutical compositions containing the presently described adropin polypeptide, derivative thereof, or polynucleotide encoding thereof as the active ingredient can be prepared according to conventional pharmaceutical compounding techniques. See, for example, Remington's Pharmaceutical Sciences, 18t$^h$ Ed., Mack Publishing Co., Easton, Pa. (1990). See also, Remington: The Science and Practice of Pharmacy, 21st Ed., Lippincott Williams & Wilkins, Philadelphia, Pa. (2005). In some embodiments, the pharmaceutical composition comprises one or more adropin stimulating agent as the active ingredient.

In one embodiment, compositions including the preparation of the present invention formulated in a compatible pharmaceutical carrier are prepared, placed in an appropriate container, and labeled for treatment of an indicated condition.

In one embodiment, a composition comprising the adropin stimulating agent of the present invention is presented in a pack or dispenser device, such as an FDA approved kit, which contain one or more unit dosages forms containing the active ingredient. In one embodiment, the pack, for example, comprises metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

Any concentration ranges, percentage range, or ratio range recited herein are to be understood to include concentrations, percentages or ratios of any integer within that range and fractions thereof, such as one tenth and one hundredth of an integer, unless otherwise indicated.

Any number range recited herein relating to any physical feature, such as tumor size, are to be understood to include any integer within the recited range, unless otherwise indicated.

In another embodiment, the pharmaceutical compositions of the invention may be formulated in the form of a pharmaceutically acceptable salt of the adropin stimulating agents of the present invention or their analogs, or derivatives thereof. In another embodiment, pharmaceutically acceptable salts include those salts formed with free amino groups such as salts derived from non-toxic inorganic or organic acids such as hydrochloric, phosphoric, acetic, oxalic, tartaric acids, and the like, and those salts formed with free carboxyl groups such as salts derived from non-toxic inorganic or organic bases such as sodium, potassium, ammonium, calcium, ferric hydroxides, isopropylamine, triethylamine, 2-ethylamino ethanol, histidine, procaine, and the like.

As used herein, the term "carrier" refers to a diluent, adjuvant, excipient, or vehicle with which the therapeutic compound is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerin, propylene glycol or other synthetic solvents. Water may be a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfate; and agents for the adjustment of tonicity such as sodium chloride or dextrose are also envisioned. The carrier may comprise, in total, from about 0.1% to about 99.99999% by weight of the pharmaceutical compositions presented herein.

As used herein, the term "pharmaceutically acceptable" means suitable for administration to a subject, e.g., a human.

For example, the term "pharmaceutically acceptable" can mean approved by a regulatory agency of the Federal or a state government or listed in the U. S. Pharmacopeia or other generally recognized pharmacopeia for use in animals, and more particularly in humans.

In another embodiment, the compositions of the invention take the form of solutions, suspensions, emulsions, powders, sustained-release formulations and the like. Such compositions will contain a therapeutically effective amount of the adropin stimulating agent of the invention, preferably in a substantially purified form, together with a suitable amount of carrier so as to provide the form for proper administration to the subject.

According to an embodiment of the invention, pharmaceutical compositions contain 0.1%-95% of the adropin stimulating agent(s) of the present invention, derivatives, or analogs thereof. According to another embodiment of the invention, pharmaceutical compositions contain 1%-70% of the adropin stimulating agent(s) derivatives, or analogs thereof. According to another embodiment of the invention, the composition or formulation to be administered may contain a quantity of adropin stimulating agent(s), derivatives, or analogs thereof, according to embodiments of the invention in an amount effective to treat the condition or disease of the subject being treated.

An embodiment of the invention relates to adropin stimulating agent of the present invention, derivatives, or analogs thereof, presented in unit dosage form and prepared by any of the methods well known in the art of pharmacy. In an embodiment of the invention, the unit dosage form is in the form of an ampoule, vial or pre-filled syringe. In addition, in vitro assays may optionally be employed to help identify optimal dosage ranges. The precise dose to be employed in the formulation will also depend on the route of administration, and the nature of the disease or disorder, and should be decided according to the judgment of the practitioner and each patient's circumstances. Effective doses can be extrapolated from dose-response curves derived from in-vitro or in-vivo animal model test bioassays or systems.

As used herein, the terms "administering", "administration," and like terms refer to any method which, in sound medical practice, delivers a composition containing an active agent to a subject in such a manner as to provide a therapeutic effect.

Depending on the location of the tissue of interest, the adropin stimulating agent of the present invention can be administered in any manner suitable for the provision of the adropin stimulating agent to cells within the tissue of interest. Thus, for example, a composition containing the adropin stimulating agent of the present invention can be introduced, for example, into the systemic circulation, which will distribute the adropin stimulating agent to the tissue of interest.

In some embodiments, the pharmaceutical compositions comprising the adropin stimulating agent is administered via intraperitoneal route of administration.

In some embodiments, the pharmaceutical compositions comprising the adropin stimulating agent is administered via transdermal, subcutaneous, intramuscular, or intravenous routes of administration. The route of administration of the pharmaceutical composition will depend on the disease or condition to be treated. Suitable routes of administration include, but are not limited to, parenteral injections, e.g., intradermal, intravenous, intramuscular, intralesional, subcutaneous, intrathecal, and any other mode of injection as known in the art. Although the bioavailability of adropin stimulating agent administered by other routes can be lower than when administered via parenteral injection, by using appropriate formulations it is envisaged that it will be possible to administer the compositions of the invention via transdermal, oral, rectal, vaginal, topical, nasal, inhalation and ocular modes of treatment. In addition, it may be desirable to introduce the pharmaceutical compositions of the invention by any suitable route, including intraventricular and intrathecal injection; intraventricular injection may be facilitated by an intraventricular catheter, for example, attached to a reservoir.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes.

According to some embodiments, the adropin stimulating agent of the present invention, derivatives, or analogs thereof can be delivered in a controlled release system. In another embodiment, an infusion pump can be used to administer the adropin stimulating agent such as the one that is used, for example, for delivering insulin or chemotherapy to specific organs or tumors. In another embodiment, the adropin stimulating agent of the invention is administered in combination with a biodegradable, biocompatible polymeric implant, which releases the adropin stimulating agent over a controlled period of time at a selected site. Examples of preferred polymeric materials include, but are not limited to, polyanhydrides, polyorthoesters, polyglycolic acid, polylactic acid, polyethylene vinyl acetate, copolymers and blends thereof (See, Medical applications of controlled release, Langer and Wise (eds.), 1974, CRC Pres., Boca Raton, Fla., the contents of which are hereby incorporated by reference in their entirety). In yet another embodiment, a controlled release system can be placed in proximity to a therapeutic target, thus requiring only a fraction of the systemic dose.

The presently described adropin stimulating agent, derivatives, or analogs thereof may also be contained in artificially created structures such as liposomes, ISCOMS, slow-releasing particles, and other vehicles which increase the half-life of the peptides or polypeptides in serum. Liposomes include emulsions, foams, micelles, insoluble monolayers, liquid crystals, phospholipid dispersions, lamellar layers and the like. Liposomes for use with the presently described peptides are formed from standard vesicle-forming lipids which generally include neutral and negatively charged phospholipids and a sterol, such as cholesterol. The selection of lipids is generally determined by considerations such as liposome size and stability in the blood. A variety of methods are available for preparing liposomes as reviewed, for example, by Coligan, J. E. et al, Current Protocols in Protein Science, 1999, John Wiley & Sons, Inc., New York, and see also U.S. Pat. Nos. 4,235,871, 4,501,728, 4,837,028, and 5,019,369.

The compositions also include incorporation of the active material into or onto particulate preparations of polymeric compounds such as polylactic acid, polglycolic acid, hydrogels, etc., or onto liposomes, microemulsions, micelles, unilamellar or multilamellar vesicles, erythrocyte ghosts, or spheroplasts). Such compositions will influence the physical state, solubility, stability, rate of in vivo release, and rate of in vivo clearance.

Kits

In some embodiments, the present invention is directed to a kit for diagnosing or prognosing liver metastases in a subject, comprising a molecular probe having specific affinity to adropin polypeptide, or a polynucleotide sequence encoding the adropin polypeptide.

In some embodiments, the kit comprises a molecular probe having specific affinity to the endogenous adropin polypeptide, or to the endogenous polynucleotide sequence encoding thereof.

In some embodiments, the kit comprises a molecular probe comprising a detection signal moiety. In some embodiments, the kit comprises an antibody. In some embodiments, the kit comprises a complementary DNA, RNA, or LNA polynucleotide, or a combination thereof. In some embodiments, the detection signal moiety is designed to generate a chemically and/or a physically detectable reaction. (e.g., an Fc binding domain of a secondary antibody).

The phrase "molecular probe", refers herein to a molecule possessing a high affinity to (i.e., an equilibrium dissociation constant values of $K_d \leq 10^{-9}$ M), in a biologically relevant system (e.g., in vitro, ex vivo or in vivo).

The phrase "detection signal moiety", is a chemical group or a molecular motif possessing medium to high affinity towards a molecular reagent or a biomolecule that induces or mediates a reaction that yields a product, that can be monitored instrumentally.

In one embodiment, the kit as described herein comprises a PCR buffer. In one embodiment, a PCR buffer comprises: 5 to 100 mM Tris-HCl and 20 to 100 mM KCl. In one embodiment, a PCR buffer further comprises 10 to 100 mM Magnesium Chloride. In one embodiment, the kit as described herein comprise a dNTP mixture. In one embodiment, the kit as described herein comprise DNA Polymerase such as but not limited to Taq DNA Polymerase. In one embodiment, the kit as described herein comprise distilled water. In one embodiment, a kit as described herein comprises a thermostable DNA polymerase.

In some embodiments, the kit provides reagents and/or buffers, such as hybridization or binding buffer, for improving binding of the molecular probe to the adropin polypeptide or polynucleotide encoding thereof. In some embodiments, the kit further provides reagents and/or buffers for detecting binding of the molecular probe to the adropin polypeptide or polynucleotide encoding thereof. In some embodiments, the antibody is conjugated to a dye molecule. In some embodiments, the antibody is conjugated to an enzyme, non-limiting examples of which comprise alkaline phosphatase and horse radish peroxidase. In some embodiments, detection buffers comprises an enzyme's specific substrate. In some embodiments, the enzyme catalyzes a reaction on the substrate giving rise to a detectable product. In some embodiments, the product is soluble or insoluble. Non-limiting examples of substrates include, but are not limited to, CDP star, NPP, NBT-BCIP, and others, all which would be apparent to one of ordinary skill in the art.

In some embodiments, the kit further comprises a control sample comprising a tissue sample of a non-afflicted subject, including but not limited to, a liver sample or a bodily fluid sample, blood for example.

In some embodiments, the components of the kit disclosed above are sterile. As used herein, the term "sterile" refers to a state of being free from biological contaminants. Any method of sterilization is applicable and would be apparent to one of ordinary skill in the art.

In some embodiments, the components of the kit are packaged within a container.

In some embodiments, the container is made of a material selected from the group consisting of thin-walled film or plastic (transparent or opaque), paperboard-based, foil, rigid plastic, metal (e.g., aluminum), glass, etc.

In some embodiments, the content of the kit is packaged, as described below, to allow for storage of the components until they are needed.

In some embodiments, some or all components of the kit may be packaged in suitable packaging to maintain sterility.

In some embodiments, the components of the kit are stored in separate containers within the main kit containment element e.g., box or analogous structure, may or may not be an airtight container, e.g., to further preserve the sterility of some or all of the components of the kit.

In some embodiments, the kit comprises instructions for contacting a sample of a subject with the molecular probe. In some embodiments, the kit comprises instructions for detecting the adropin polypeptide, or a polynucleotide sequence encoding the adropin polypeptide in the sample. In some embodiments, the kit comprises instructions for and determining the expression level of the adropin polypeptide, or a polynucleotide sequence encoding the adropin polypeptide in the sample compared to a control sample.

In some embodiments, the kit comprises instructions for: contacting a sample of a subject with the molecular probe, detecting the adropin polypeptide, or a polynucleotide sequence encoding the adropin polypeptide in the sample, and determining the expression level of the adropin polypeptide, or a polynucleotide sequence encoding the adropin polypeptide in the sample compared to a control sample.

In some embodiments, the instructions may be recorded on a suitable recording medium or substrate. For example, the instructions may be printed on a substrate, such as paper or plastic, etc.

In some embodiments, the instructions may be present in the kit as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In the description and claims of the present application, each of the verbs, "comprise", "include" and "have" and conjugates thereof, are used to indicate that the object or objects of the verb are not necessarily a complete listing of components, elements or parts of the subject or subjects of the verb.

Other terms as used herein are meant to be defined by their well-known meanings in the art.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

EXAMPLES

Generally, the nomenclature used herein, and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds.) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells-A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Strategies for Protein Purification and Characterization-A Laboratory Course Manual" CSHL Press (1996); all of which are incorporated by reference. Other general references are provided throughout this document.

Materials and Methods

Cell Culture

All cell lines were maintained in DMEM medium supplemented with 10% FCS, 1% Penicillin/Streptomycin and 1% L-Glutamine in 10 cm$^2$ plates in 5% humidified CO2 at 37° C. Twice a week cells were passaged. Detaching was done for MC-38, CT26 and normal cells by incubation with 1 ml trypsin for 2-3 min and then seeded (usually 1:10) in 10 ml DMEM supplemented medium which stopped the enzymatic process of trypsin. EL4 cells are grown in suspension, thus not requiring this stage. For the experiments, after the trypsin detachment, 1 ml of cells was transferred into 13 ml medium and then the cells were centrifuged (1,400 rpm, 10 min, room temperature (RT)) and resuspended in 1 ml of fresh medium (for in vitro experiments) or sterile PBS×l (for mouse injections in vivo). Cells were counted in a hemocytometer under a light microscope (magnification×10) immediately after the addition of Trypan blue solution (1:1 ratio). Non-stained cells were considered viable. For in-vivo mouse injections, the cells were diluted in sterile PBS xl to a final concentration of $5\times10^4$ for MC-38 cells or $5\times10^5$ for EL-4 cells per 100 μl. For XTT in vitro experiments, the cells were seeded in a 96-well plate (100 μl per well) in the morning and in the afternoon (once the cells adhered) the medium was changed according to the treatment (DMEM, Adropin 25 ng/ml, Adropin 50 ng/ml or Adropin 100 ng/ml). On the following day, the XTT reaction solution was added to the wells according to the cell proliferation kit (XTT based; Biological Industries, Israel) and the plate was read 2, 3 and 4 hours following, using a Magellan for Infinite F50 (Tecan, Switzerland) microplate reader at 450 nm.

In-Vivo Mice Experiments

Animal experiments were performed according to a protocol approved by the Animal Care Committee of the Hebrew University. All mice were kept in a specific pathogen-free facility and were handled according to the criteria outlined in the "Guide for the Care and Use of Laboratory Animals" prepared by the National Academy of Sciences and published by the National Institutes of Health.

Naïve mice—At two and five months of age the mice were anesthetized (n=10/group), a blood sample was withdrawn (~1 ml) and then the mice were sacrificed, and their livers were excised. Liver samples were divided while one part was fixed in 4% (v/v) buffered formalin (Bio-Lab Ltd., Jerusalem, Israel) for histological evaluation and the rest was snap-frozen in liquid nitrogen for further analysis. For 5-bromo-2'-deoxyuridine (BrdU) analysis the mice were injected i.p. with BrdU (Sigma-Aldrich, Rehovot, Israel)—0.1 mg BrdU/1 gr body weight of mice at a concentration of 10 mg/ml in saline 3 hours prior to sacrifice.

Metastases model—In order to obtain metastases in the liver, a well-documented model was employed using the cancer cell lines derived from C57Bl/6 mice—MC-38 or EL-4 cells. The cancer cells were injected intra-splenic into MDR2-Knockout (KO) and C57Bl/6 mice at two and five months of age, and after 5 minutes the spleen was removed to prevent the development of a primary tumor in the spleen. Fourteen days later, the mice were euthanized, and their livers were removed in a similar manner to that described above.

Adropin injection—The adropin peptide (corresponding to amino acids at positions 34-76) was purchased from ChinaPeptides Co., Ltd. with a purity of >95%. The peptide was injected to mice according to two protocols. For the first protocol, termed 'short adropin treatment', adropin was injected at 450 nmole/kg in saline (80 μl injected), i.p., twice daily, for the five days surrounding the MC-38 CRC cell injection. For the second protocol, termed 'prolonged adropin treatment', 450 nmole/kg of adropin was injected i.p. (100 μl injected) once every three days from the morning of MC-38 cell injection throughout the experiment until the mice were sacrificed fourteen days later (a total of five injections).

Metastases Quantification

Formalin-fixed paraffin-embedded tissue slides were stained with hematoxylin-eosin (H&E) staining and analyzed under a microscope using Cellsens Entry software (Olympus, Japan). The number and size of metastases larger than 4,000 μm$^2$ were recorded. The number of metastases was normalized relatively to the size of the liver sample analyzed.

RNA Isolation

RNA extraction was performed from snap-frozen tissues using the miRNeasy Micro Kit (Qiagen, Hilden, Germany) and its quantity and integrity were checked using Nanodrop (ND spectrophotometer, Wilmington, Del., USA) or TapeStation (Agilent, Calif., USA).

RNA Sequencing

For RNA sequencing, the library preparation was performed using the Illumina TrueSeq RNA Sample Preparation Kit at The Center for Genomic Technologies at Edmond J. Safra Campus. It was sequenced using Illumina's NextSeq machine with single end 80 bp expected reads. The following analyses were performed: Cutadapt, TopHat, HTSeq, Cufflinks, DESeq2 and VennDiagram (assisted by the Bioinformatics Unit at Ein Kerem).

Protein Extraction

Protein extraction was performed from snap-frozen tissues kept at −80° C. Around 30 mg of tissue was added into 500 μl containing: PBS×1, 1 mg/ml Pepstatin A (Tocris Bioscience, UK) and 1 mg/ml Protease Inhibitor Cocktail Set I (Calbiochem, Calif., US). The tissue was homogenized using Polytron PT2100 (Kinematica AG, Switzerland) and then 1% (v/v) of Triton x100 was added. After a short vortex the homogenized tissue was frozen overnight at −80° C. The following day the tissues were thawed, short vortex and then centrifuged in 10,000 g at 4° C., for 5 min. The supernatant was separated and aliquoted.

The concentration of the proteins was determined using Bio-Rad protein assay (Bio-Rad Laboratories, Germany). According to this method the protein was diluted 1:1,000 and the Bradford reagent was diluted 1:5 in double distilled water. The protein level was quantified by an O.D. reading at 595 nm on UltraSpec 2000 (Pharmacia Biotech, Sweden).

Adropin Enzyme Linked Immunosorbent Assay (ELISA)

Adropin levels were determined using the ELISA Kit (Cloud-Clone Corp., Texas, USA) for liver or serum mice samples according to the manufacturer's protocol. The results were analyzed using Magellan for Infinite F50 (Tecan, Switzerland).

Statistical Analysis

Unless stated otherwise, data are means±standard deviation (SD). Statistical significance was calculated with GraphPad Instat software using the Mann-Whitney test. A two-tailed p<0.05 was taken to indicate a statistically significant difference. * p<0.05, p<0.01, *p<0.0001.

Example 1

Adropin as a Diagnostic and Prognostic Biomarker for Liver Metastases

In recent years, the inventors have been examining the effect of pre-existing pathophysiological conditions on hepatic metastatic seeding and proliferation, using, inter alia, mouse models of chronic liver inflammation (chronic cholangitis modeled by genetically engineered Mdr2-KO mice) compared to their wild-type counterparts (C57BL/6) at different ages. In preliminary experiments, the MC38 murine colorectal cancer cells were injected into the control male C57/BL6 mice or to age matched male Mdr2-KO mice (two- and five-month old). Interestingly, contradictory results were obtained from two-month old compared to five-month old Mdr2-KO mice (FIG. 1). In the younger mice, the chronic inflammatory pre-existing environment reduced colorectal liver metastases (CRLM) metastatic seeding (p=0.009), while, in the older mice, the pre-existing environment accelerated CRLM metastatic seeding (P=0.049).

Figure 2A:
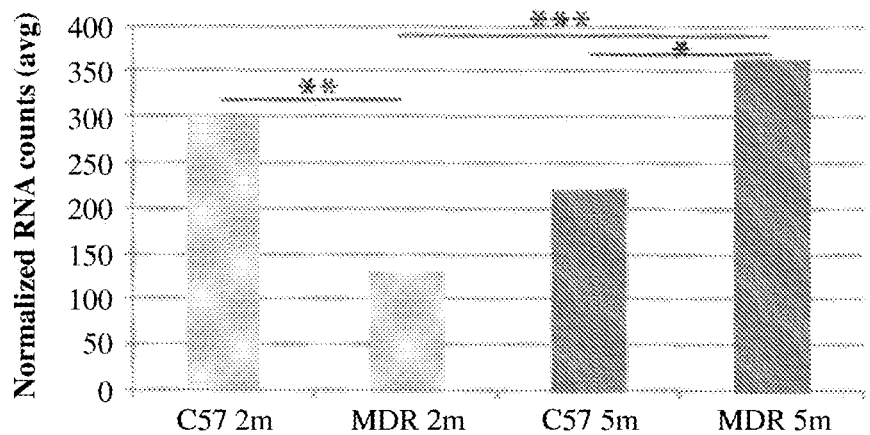
FIGS. 2A-2B are bar graphs depicting the average RNA levels of Nrp2 (A) and Enho (B) for each strain and age. *p<0.1, p<0.01, *p<0.0001.
Figure 2B:
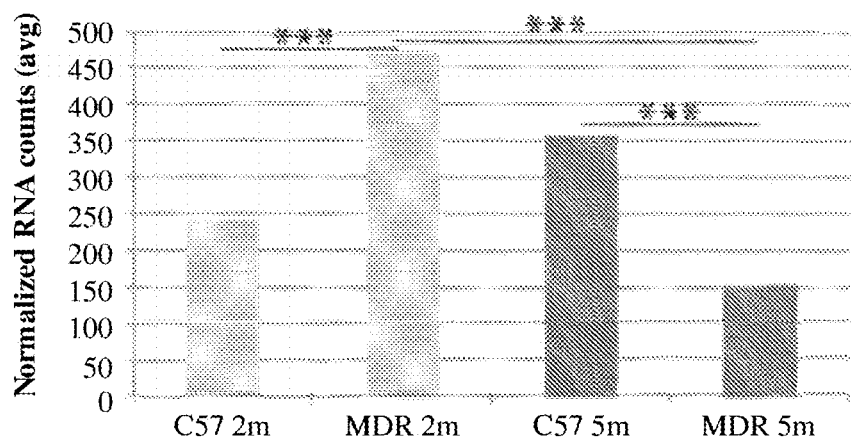

In order to search for possible candidates that play a role in protecting the liver in two months old MDR2-KO mice compared to the other groups, liver samples from three naïve mice (which did not receive an injection of MC38 cancer cells or any other treatment) were taken from each group. RNA extraction and sequencing was performed on these 12 samples and a bioinformatic analysis was performed. Two genes stood out as having a positive or negative correlation to the number of metastases in each group. While Nrp2 had a positive correlation with the number of metastases in each experimental group, Enho had an inverse correlation (FIGS. 2A-2B). Enho is the gene encoding an mRNA which is translated into the adropin protein.

Figure 3:
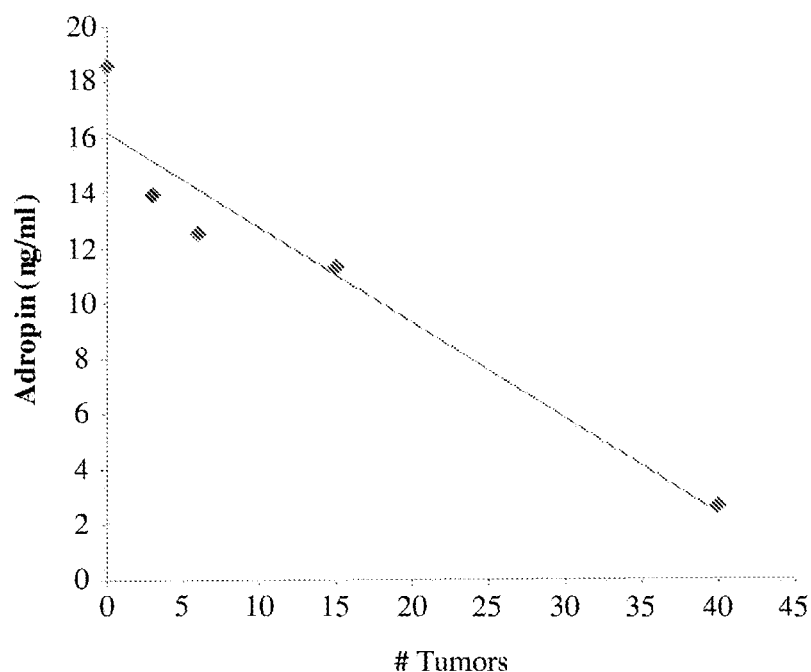
FIG. 3 is a graph depicting the correlation of adropin (ng/ml) levels, as tested by enzyme linked immunosorbent assay, relative to the number of tumors within each liver sample; $R^2=0.921$.

Surprisingly, the Enho mRNA levels negatively correlated (correlation coefficient=−0.99) with the number of tumors in each experimental group. An ELISA assay was conducted on the adropin protein found in naïve livers to substantiate this finding on an additional level and found a negative correlation with the number of tumors in each experimental group (correlation coefficient=−0.95). Further examined were the adropin levels in livers with colorectal liver metastases, which found a strong negative correlation between the two ($R^2$=0.915) (FIG. 3).

This result showed the potential of adropin as a prognostic marker. The example above shows the inverse relation of adropin encoding gene expression level (i.e., Enho) and cancerous prognosis.

Example 2

Therapeutic Effect of Adropin on Liver Metastases

Figure 4A:
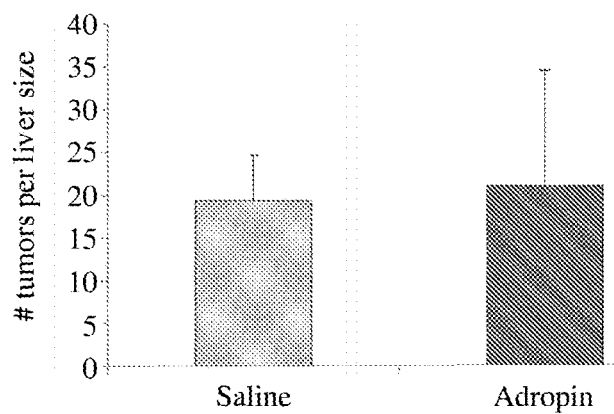
FIGS. 4A-4B are bar graphs depicting the in-vivo preventive effect of adropin injection (450 nmol/kg/i.p) on the number of liver metastases (A) and tumor size (B). **p<0.01.
Figure 4B:
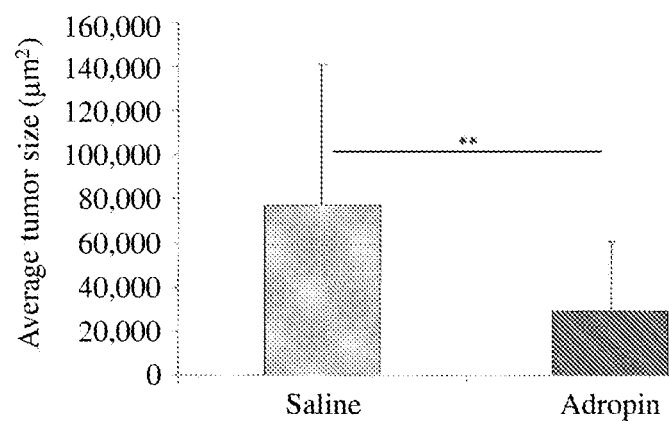

A synthetic peptide of adropin (34-76 aa, purity: >95%) was then used to validate the findings regarding adropin's role in protecting the liver from metastases. The peptide, or saline as control, was injected (450 nmol/kg/i.p.) to mice during the week of cancer cell injection (2 days before, day of tumor cell injection and the following two days). A significant decrease of over 2.5-fold in the metastases size was observed, in the adropin-injected mice (FIG. 4B).

Figure 5A:
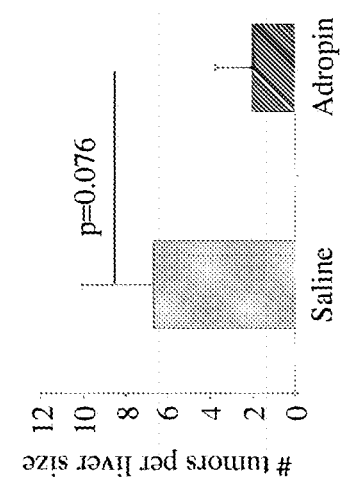
FIGS. 5A-5B are bar graphs depicting the in-vivo effect of continuous adropin treatment (450 nmol/kg/i.p) in reducing the number of liver metastases (A) and tumor size (B).
Figure 5B:
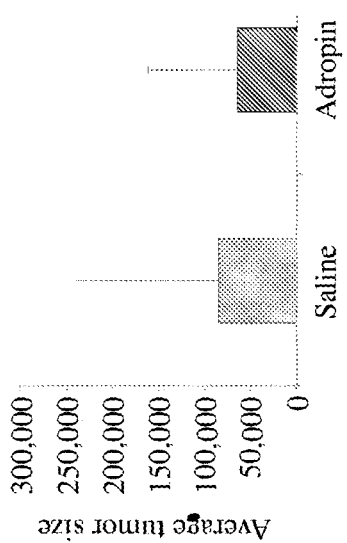

While no differences in BrdU levels were found in the hepatic parenchyma, there was a decrease in the number of BrdU stained cells in the tumors of the mice which were administered with adropin. A further protocol was employed where adropin was injected every 3 days throughout the entire experiment period (14 days), starting from the morning of the cancer cell injection. As shown (FIGS. 5A-5B), the number and size of metastases have been reduced upon adropin injections (marginally significant). These in vivo experiments showed the feasibility of adropin use in reducing the number and size of liver metastases.

Figure 6A:
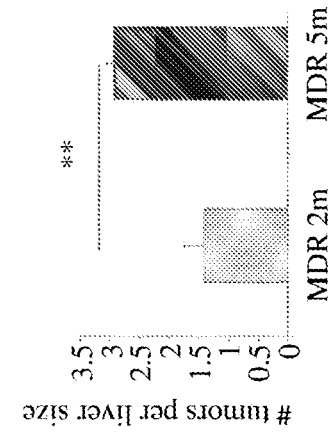
FIGS. 6A-6B are bar graphs showing reduced number (A) and size (B) of lymphoma metastases to liver in two-month-old MDR2-KO mice. **p<0.01.
Figure 6B:
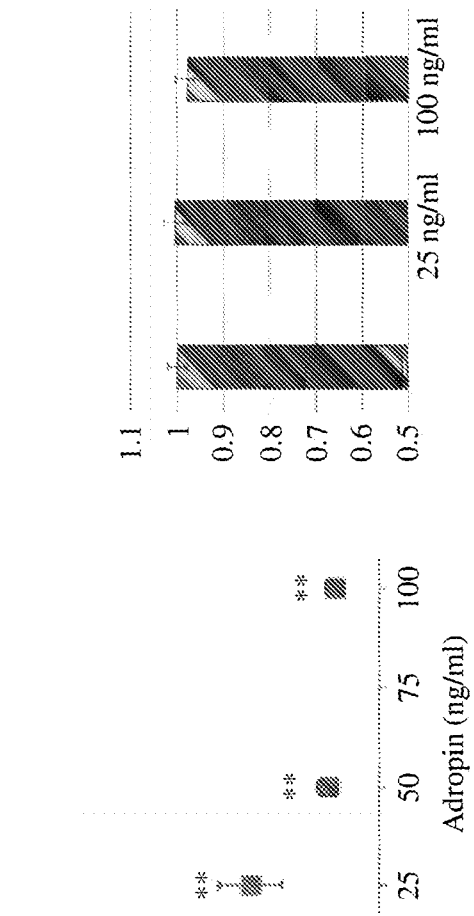

Additionally, EL4 mouse T cell lymphoma cells were injected according to a similar protocol to MDR2-KO mice at 2 and 5 months of age. For the two months old mice, it was found that there were significantly less, and smaller metastases as compared to their 5 months old counterparts (FIGS. 6A-6B). Due to the similarity of results to those found in the MC38 cells, adropin was suggested as a possible effective treatment for additional tumor types which send metastases to the liver.

The present example shows the anti-metastatic effect of adropin and suggests its potential use as an anti-cancer drug.

Example 3

Adropin Specifically Reduces Proliferation of Cancer Cells In-Vitro

Figure 7:
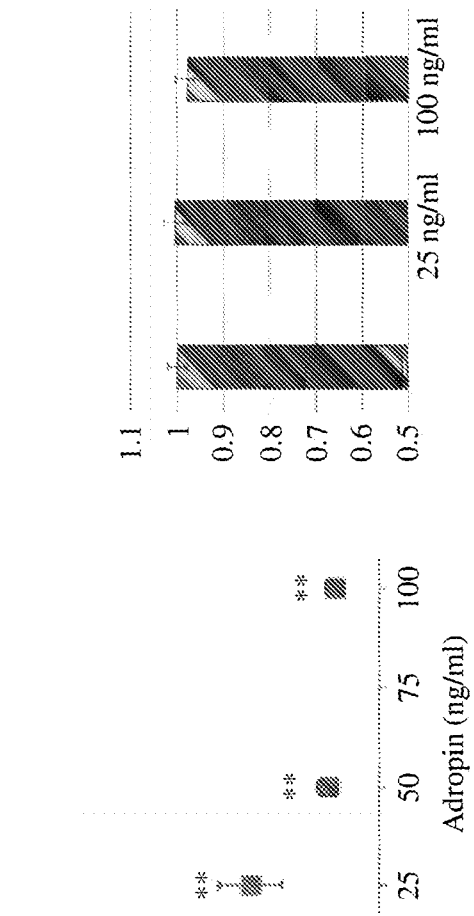
FIG. 7 is a graph showing that adropin reduces cell proliferation in vitro. XTT MC-38 (colorectal cancer cell line) cell-proliferation tests were performed with different adropin concentrations supplemented to the cell culture media (25, 50, 75 and 100 ng/ml). **p<0.01.

To test adropin's direct effects on MC-38 cells, XTT cell-proliferation tests were performed with adropin added to the medium at different concentrations (25-100 ng/ml). The addition of the secreted part of adropin (34-76 aa) induced a decrease in the proliferation levels of the colorectal cancer cells in a dose dependent manner (FIG. 7).

Figure 8A:
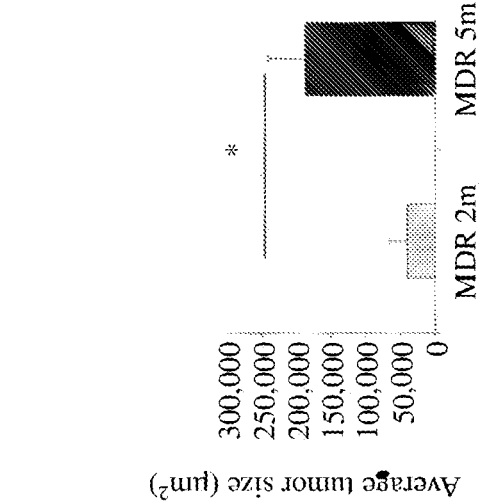

The inhibitory effect of adropin on cancer cells was significantly higher when the cancer cells were seeded at low concentrations (FIGS. 8B-8C; $5 \times 10^3$ and $1 \times 10^3$ cells/well in a 96 well plate), whereas almost no effect was detected for higher cell concentrations (FIG. 8A; $5 \times 10^4$ cells/well in a 96 well plate).

A limitation of the XTT assay is that it cannot differentiate the effects attributed to the cells' total number (e.g., proliferation) from the cells' metabolic activity. Accordingly, the inventors performed direct cell count analyses. Adropin was shown to have even higher inhibitory effect on the number of MC38 cells (FIGS. 9A-9B) at all of the tested seeding concentrations (up to $5 \times 10^4$ cells/well in a 96 well plate). The inventors further tested these effects in another colorectal cancer cell—CT26, which provided similar results (FIGS. 9C-9D). The inventors further tested these effects in a different cancer type—the breast cancer cell line 4T1, which provided similar results.

To test adverse effects (i.e., level of specificity) of adropin on proliferating cancer cells, the inventors examined its effect on normal cells. No detectable effects of adropin treatment was observed in normal fibroblasts, kidney cells, or hepatocytes in-vitro (FIGS. 10A-10C).

Example 4

Adropin Stability Assessment

The inventors then examined the stability of adropin in vitro. For that, the inventors had set up a liquid chromatography mass spectrometry (LC-MS) assay and used it to examine the stability of adropin under different storage conditions (see Table 1). The inventors found that adropin was highly stable even when dissolved in saline either at −20° C. or −80° C., for as long as up to one month. Contrary, approximately 50% degradation were observed when the dissolved peptide was stored at a room temperature for one month.

| Procedure | Concentration obtained by LC-MS (ng/ml) |
|---|---|
| −80° C. for 1 month | 95 |
| −20° C. for 1 month | 95 |
| 4° C. for 1 month | 84 |
| Room temperature (RT) for 1 month | 55 |
| Freeze/Thaw cycle × 3 (−20° C. to RT once a week) | 92 |
| −80° C. and then −20° C. for 1 week | 100 |
| −80° C. and then 4° C. for 1 week | 99 |
| −80° C. and then RT for 1 week | 94 |

The next step was to assess the stability of adropin during incubation with human or mouse serum. The inventors found that adropin was extremely stable as its level remained at 55% even after 24 hours incubation with mouse serum (FIG. 11).

Example 5

The Adropin Therapeutic Window In Vivo

Due to the observation that a treatment given only during the first 4 days had a sustained effect on tumor progression, the inventors had decided to analyze the possibility of a feedback mechanism and self-production of the adropin protein by the liver, which was induced by the injection of the synthetic adropin in-vivo. C57BL/6 mice were given a single injection of adropin at different concentrations and sacrificed at varied times afterward. A large increase of both adropin RNA and protein levels were detected in the liver which lasting for two days (FIGS. 12A-12B). The lower concentration induced higher effect.

Based on the results demonstrating the high hepatic levels of the peptide over time following a single injection, an additional in-vivo experiment was carried out using an alternative schedule for the adropin injections throughout the two weeks period. The mice were injected every two days with adropin (0.01 or 0.05 mg/i.p. injection) or saline starting from the morning of the MC-38 cell injection until being sacrificed two weeks later. The inventors demonstrated that this protocol provided significantly improved effects on both the number and size of hepatic metastases (FIGS. 13A-13B).

Example 6

Optimization of Adropin Administration

Figure 14:
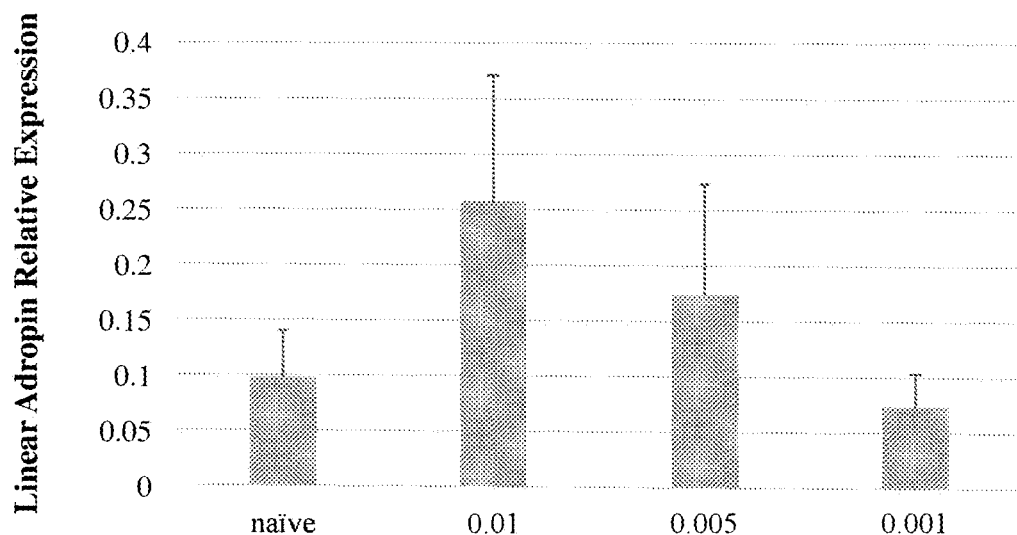
FIG. 14 is a vertical bar graph showing the dose effects of a single adropin administration (i.p.) at the indicated doses (0 (naïve), 0.01 mg, 0.05 mg and 0.001 mg) on hepatic adropin RNA levels (measured by qRT-PCR). Each group comprised 4 mice.

The inventors then pursued optimization of adropin administration. With this respect, different doses of adropin were administered to mice and hepatic adropin RNA levels were quantified (FIG. 14). Adropin administered at a dose of 0.01 mg was found to substantially increase hepatic adropin mRNA levels. Reduction in the dose of the administered adropin led to a reduction in the administered adropin effect. While 0.005 mg still induced some increase in hepatic adropin mRNA levels, a dose of 0.001 mg did not induce such an effect (comparable to control).

Figure 15:
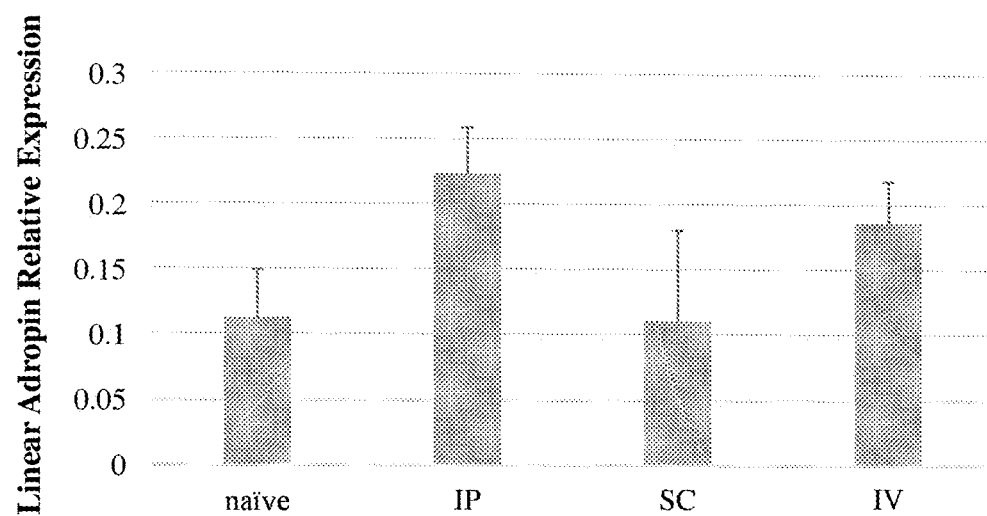
FIG. 15 is a vertical bar graph showing the efficacy of different adropin routes of administration on hepatic adropin RNA in naïve mice (measured by qRT-PCR). Adropin was injected at a dose 0.01 mg. Naïve, non-injected; IP, intraperitoneal injection; SC, subcutaneous injection; IV, intravenous injection.

Further, the inventors examined whether the administration route of the adropin affects the hepatic adropin mRNA levels (FIG. 15). Intraperitoneal injection resulted in the greatest increase of hepatic adropin mRNA levels, while intravenous injection also resulted in a substantial increase. Subcutaneous injection of adropin to naïve mice did not seem to increase the hepatic adropin mRNA levels (comparable to control).

While certain features of the invention have been described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method for treating a subject afflicted with cancer in an adropin-expressing organ, comprising administering to said subject a therapeutically effective amount of an adropin stimulating agent, wherein said agent increases the levels of expressed adropin in said subject, and wherein said agent is an adropin polypeptide comprising SEQ ID NO: 1 (CHSR-SADVDSLSESSPNSSPGPCPEKAPPPQKPSHEG-SYLLQP) or SEQ ID NO: 1 with up to two substitutions, insertions, or deletions, thereby treating the subject afflicted with cancer in an adropin-expressing organ.

2. The method of claim 1, wherein said cancer is metastatic cancer.

3. The method of claim 2, wherein said metastatic cancer is liver metastases.

4. The method of claim 1, wherein said increased adropin expression levels comprise increased RNA transcript levels, increased protein production levels, increased protein secretion levels, or any combination thereof.

5. The method of claim 1, wherein said treating comprises decreasing tumor size, decreasing metastases frequency, or a combination thereof.

6. The method of claim 1, further comprising the step of monitoring one or more symptoms selected from the group consisting of: tumor size, tumor growth, number of metastases, and size of metastases.

* * * * *